United States Patent [19]

Kohama et al.

[11] Patent Number: 5,789,595
[45] Date of Patent: Aug. 4, 1998

[54] TETRAHYDROISOQUINOLINE DERIVATIVE AND MEDICAL PREPARATION CONTAINING THE SAME

[75] Inventors: Hiromasa Kohama; Nobuyuki Nakata; Masahiro Suzuki; Youko Terajima, all of Kanagawa, Japan

[73] Assignee: Terumo Kabushiki Kaisha, Tokyo, Japan

[21] Appl. No.: 836,521

[22] PCT Filed: Oct. 26, 1995

[86] PCT No.: PCT/JP95/02201

§ 371 Date: Jul. 21, 1997

§ 102(e) Date: Jul. 21, 1997

[87] PCT Pub. No.: WO96/13497

PCT Pub. Date: May 9, 1996

[30] Foreign Application Priority Data

Nov. 1, 1994 [JP] Japan .................. 6-269146
May 8, 1995 [JP] Japan .................. 7-109194

[51] Int. Cl.$^6$ .................. C07D 217/00; A61K 31/42
[52] U.S. Cl. .................. 546/143; 514/310
[58] Field of Search .................. 546/143; 514/310

[56] References Cited

FOREIGN PATENT DOCUMENTS

| | | |
|---|---|---|
| 0 372 486A2 | 5/1989 | European Pat. Off. . |
| 0 445 796A2 | 7/1991 | European Pat. Off. . |
| 0 512 831A1 | 7/1992 | European Pat. Off. ...... C07D 401/06 |
| 0 513 675A1 | 8/1992 | European Pat. Off. . |
| 512831 | 11/1992 | European Pat. Off. ...... C07D 401/06 |

OTHER PUBLICATIONS

Phillips et al., Blood, vol. 71, 831–843 (1988).
M. Folkmann et al., Synthesis, 1159 (1990).
H.C. Brown et al., Journal of Organic Chemistry, vol. 50, 1582–9 (1985).
H.H. Friedman (Tetrahedron Letters No. 38, 3251 (1975).
Ajao, J.F. et al., Journal of Heterocyclic Chemistry, vol. 22, 329–31 (1985).
Paul, R. et al., Journal of Medicinal Chemistry, vol. 15, 720–6 (1972).

Primary Examiner—S. Mark Clardy
Assistant Examiner—Sabiha N. Qazi
Attorney, Agent, or Firm—Burns, Doane, Swecker & Mathis, LLP

[57] ABSTRACT

The present invention relates to a tetrahydroisoquinoline derivative represented by the following formula 1 exhibiting an inhibitory action for agglutination caused by fibrinogen, which may be effectively used as an antithrombotic agent or a platelet agglutination-inhibiting agent. The present invention also relates to a medical preparation containing such compound.

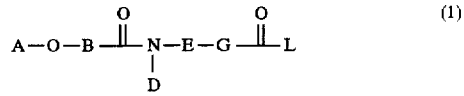

In formula 1, B and G are an alkylene optionally substituted with an alkyl or the like; D is H, an alkyl, or the like; E is 1,2,3,4-tetrahydroisoquinoline optionally substituted with $R_1$ to $R_4$ which binds to G at position 2; $R_1$ to $R_4$ are an alkyl or the like; L is hydroxy or the like; and A is a substituent represented by formula (2), and C is carbon.

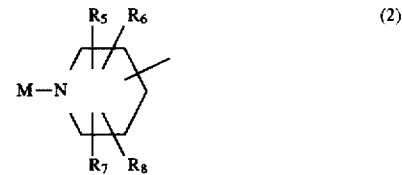

In formula 2, M and $R_5$ to $R_8$ are H, an alkyl or the like.

10 Claims, No Drawings

TETRAHYDROISOQUINOLINE DERIVATIVE AND MEDICAL PREPARATION CONTAINING THE SAME

TECHNICAL FIELD

The present invention relates to a novel tetrahydroisoquinoline derivative and a medical preparation containing the same.

BACKGROUND ART

Agglutination of platelets plays a significant role in the formation of thrombus and blood coagulation. In the final stage of the platelet agglutination, GPIIb/IIIa receptor on the surface of platelets is activated before its binding to fibrinogen. Therefore, an agent capable of inhibiting the binding of the GPIIb/IIIa receptor with the adhesive protein like fibrinogen should be useful in preventing the formation of the thrombus and the blood coagulation. The active site for the binding of the GPIIb/IIIa receptor and the fibrinogen has been reported to be Arg-Gly-Asp-Ser (RGDS) of the fibrinogen (Phillips et al., Blood, vol. 71, 831–843 (1988)). In view of such finding, RGDS analogues have been developed for use as an antagonist for the GPIIb/IIIa receptor (Patent Publications: EP 512831, EP 445796, EP 372486, and EP 513675). There is a demand for a highly active antagonist which exhibits excellent oral absorption.

DISCLOSURE OF THE INVENTION

An object of the present invention is to provide a tetrahydroisoquinoline derivative which has an activity to compete with GPIIb/IIIa receptor, and hence, which exhibits platelet agglutination-inhibitory action and antithrombotic action; and medical preparations such as platelet agglutination-inhibitory agent, fibrinogen receptor-inhibitory agent and antithrombotic agent which contain the tetrahydroisoquinoline derivative as their effective component.

More illustratively, the present invention is directed to a novel tetrahydroisoquinoline derivative having the structure as shown in Formula 1:

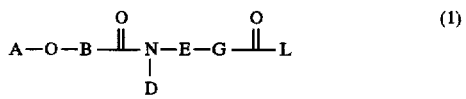

In formula 1, B and G independently represent a (C: 0–10) alkylene optionally substituted with a substituent (said substituent being a (C: 1–10) alkyl, an aryl (C: 0–8) alkyl, a (C: 0–10) alkylamino, an acylamino, a (C: 1–10) alkoxy, an aryl (C: 0–8) alkoxy, an (aryl (C: 0–8) alkyl)amino, hydroxy, or halogeno);

D represents hydrogen, a (C: 1–10) alkyl, a (C: 1–10) alkoxycarbonyl, or an aryl (C: 0–8) alkoxycarbonyl, a (C: 1–10) alkylcarbonyloxy (C: 1–10) alkoxycarbonyl, or an aryl (C: 0–10) alkylcarbonyloxy (C: 1–10) alkoxycarbonyl; alkylcarbonyloxy (C: 1–10) alkoxycarbonyl;

E represents 1,2,3,4-tetrahydroisoquinoline optionally substituted with substituents $R_1$, $R_2$, $R_3$ and $R_4$, and which binds to G at position 2 (said substituents $R_1$, $R_2$, $R_3$ and $R_4$ independently representing a (C: 1–10) alkyl, an aryl (C: 0–8) alkyl, a (C: 0–10) alkylamino, an acylamino, a (C: 1–10) alkoxy, an aryl (C: 0–8) alkoxy, an (aryl (C: 0–8) alkyl)amino, hydroxy, or halogeno);

L represents hydroxy, a (C: 0–10) alkylamino, a di (C: 0–10) alkylamino, an (aryl (C: 1–10) alkyl)amino, a (C: 1–10) alkoxy, an aryl (C: 0–8) alkoxy, a (C: 1–10) alkylcarbonyloxy (C: 1–10) alkoxy, or an aryl (C: 1–10) alkylcarbonyloxy (C: 1–10) alkoxy;

A represents the substituent represented by formula 2 and C represents carbon.

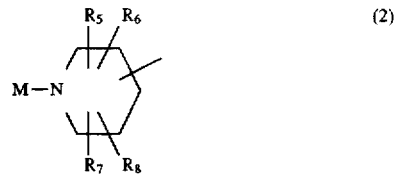

In formula 2, M represents hydrogen, a (C: 1–10) alkyl, a (C: 1–10) alkoxycarbonyl, or an aryl (C: 0–8) alkoxycarbonyl, a (C: 1–10) alkylcarbonyloxy (C: 1–10) alkoxycarbonyl, or an aryl (C: 0–10) alkylcarbonyloxy (C: 1–10) alkoxycarbonyl; and $R_5$, $R_6$, $R_7$ and $R_8$ independently represent hydrogen, a (C: 1–10) alkyl, an aryl (C: 0–8) alkyl, a (C: 0–10) alkylamino, an acylamino, (C: 1–10) alkoxy, an aryl (C: 0–8) alkoxy, hydroxy, or halogeno, and C represents carbon.

The present invention is also directed to a medical preparation containing the tetrahydroisoquinoline derivative represented by formula 1.

The present invention is also directed to a platelet agglutination-inhibitory agent containing the tetrahydroisoquinoline derivative represented by formula 1.

The present invention is also directed to an antagonist for fibrinogen receptor containing the tetrahydroisoquinoline derivative represented by formula 1.

The present invention is also directed to an antithrombotic agent containing the tetrahydroisoquinoline derivative represented by formula 1.

It should be noted that the tetrahydroisoquinoline derivative of the present invention may be used in the form of a salt.

Typical, but non-limited illustrating salts that may be formed with its acidic functional group include salts with an alkaline metal or an alkaline earth metal such as lithium, sodium, potassium, magnesium, or calcium; salts with iron, aluminum, zinc, copper, manganese, ammonium, or quaternary ammonium; and salts with a basic primary, secondary or tertiary amine such as ethylamine, propylamine, isopropylamine, cyclohexylamine, dimethylamine, diethylamine, diisopropylamine, dicyclohexylamine, pyrrolidine, piperidine, N-methylpiperidine, N-ethylpiperidine, morpholine, N-methylmorpholine, triethylamine, tripropylamine, ethylenediamine, ethanolamine, trimetamine, lysine, arginin, or histidine. Typical, but non-limited illustrating salts that may be formed with its basic functional group include salts with an inorganic acid such as hydrochloric acid, hydrobromic acid, sulfuric acid, carbonic acid, bicarbonic acid, nitric acid, or phosphoric acid; and salts with an organic acid such as acetic acid, propionic acid, butanoic acid, oxalic acid, malonic acid, succinic acid, glutaric acid, maleic acid, fumaric acid, benzoic acid, phenylacetic acid, cinammonic acid, mandelic acid, glycolic acid, lactic acid, malic acid, tartaric acid, citric acid, aspartic acid, glutamic acid, ascorbic acid, methanesulfonic acid (mesyl acid), ethanesulfonic acid, or p-toluenesulfonic acid (tosyl acid).

The compound represented by formula 1 of the present invention may be produced by the procedure as described below. In summary, the compound of formula 1 may be produced by condensing the compound of formula 3 as will be shown below and the compound of formula 4 as will be shown below by using a condensing agent optionally in the presence of a base; or by converting the compound of formula 3 into a carboxylic acid derivative such as an acid halide, an acid anhydride, an active ester, or an active amide, and condensing the product in the presence of a base or the like followed by optional cleavage of the protecting group.

Typical "condensing agents" include N,N'-dicyclohexylcarbodiimide, N,N'-diethylcarbodiimide, N,N'-diisopropylcarbodiimide, N-ethyl-N'-(3-dimethylaminopropyl)carbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, N,N'-carbonylbis-(2-methylimidazole), benzotriazole-1-yloxy-tris (dimethylamino)phosphonium hexafluorophosphate, diphenylphosphorylazide, and pentamethyleneketene-N-cyclohexylimine.

Typical "bases" include organic bases such as trimethylamine, triethylamine, and N-methylmorpholine; and inorganic bases such as sodium hydroxide, sodium carbonate, sodium bicarbonate, potassium hydroxide, potassium carbonate, potassium bicarbonate, magnesium hydroxide, magnesium carbonate, and magnesium bicarbonate.

Typical "carboxylic acid derivatives" include an acid halide such as acid chloride or acid bromide; an anhydrous mixed acid with such acid as acetic acid, propionic acid, butanoic acid, valeric acid, isobutanoic acid, isovaleric acid, pivalic acid, trichloroacetic acid, benzoic acid, methanesulfonic acid, p-toluenesulfonic acid, methyl carbonate, ethyl carbonate, propyl carbonate, butyl carbonate, or isobutyl carbonate; an active ester such as cyanomethylester, p-nitrophenylester, 2,4-dinitrophenylester, or pentafluorophenylester; and an active amide with imidazole, triazole, or the like.

The "condensation" reaction is generally carried out in such solvent as acetnitrile, dioxane, ethyl acetate, tetrahydrofuran, ether, acetone, N,N-dimethylformamide, chloroform, methylene chloride, ethylene chloride, hexane, pyridine, methanol, ethanol, and water, which may be used either alone or in combination of two or more.

The "protecting group" is a group which may be substituted to hydrogen by an appropriate reaction when M in formula 2 is a substituent other than hydrogen, and which may typically be a known protecting group such as benzyloxycarbonyl group, p-methoxybenzyloxycarbonyl group, p-nitrobenzyloxycarbonyl group, o-chlorobenzyloxycarbonyl group, t-butoxycarbonyl group, trifluoroacetyl, formyl, or the like. The protecting group is also a group which may be substituted to hydroxy by an appropriate reaction when L in formula 1 is a substituent other than hydroxy, and which may typically be a known protecting group such as methoxy, ethoxy, benzyloxy, p-nitrobenzyloxy, t-butoxy, cyclohexyloxy, or the like.

The reaction conditions for the "cleavage of the protecting group" may be selected in accordance with the type of the protecting group, for example, from acid treatment by hydrogen chloride, hydrogen bromide, hydrogen fluoride, methanesulfonic acid, trifluoromethanesulfonic acid, trifluoroacetic acid or a mixture thereof; base treatment by lithium hydroxide, sodium hydroxide, potassium hydroxide, barium hydroxide, sodium carbonate, potassium carbonate, sodium bicarbonate, potassium bicarbonate, hydrazine, diethylamine, piperidine, or the like; reduction treatment using a metal catalyst such as palladium-carbon; and the like. The reaction is generally conducted in the absence of a solvent, or in the presence of such solvent as acetnitrile, dioxane, ethyl acetate, tetrahydrofuran, ether, acetone, N,N-dimethylformamide, chloroform, methylene chloride, ethylene chloride, hexane, methanol, ethanol, isopropanol, water, and acetic acid, which may be used either alone or in combination of two or more.

Another method for synthesizing the compound of formula 1 when M in formula 2 represents a (C: 1–10) alkoxycarbonyl, an aryl (C: 0–8) alkoxycarbonyl, a (C: 1–10) alkylcarbonyloxy (C: 1–10) alkoxycarbonyl, or an aryl (C: 0–10) alkylcarbonyloxy (C: 1–10) alkoxycarbonyl comprises the step of reacting the compound of formula 1 wherein M in formula 2 is hydrogen with the corresponding carbonic acid derivative optionally in the presence of a base.

Typical "carbonic acid derivatives" include alkoxycarbonyl halides such as methoxycarbonyl chloride, ethoxycarbonyl chloride, propoxycarbonyl chloride, butoxycarbonyl chloride, pentyloxycarbonyl chloride, hexyloxycarbonyl chloride, heptyloxycarbonyl chloride, isopropoxycarbonyl chloride, isobutoxycarbonyl chloride, benzyloxycarbonyl chloride, and t-butoxycarbonyl chloride; substituted alkoxycarbonyl halides such as (acetoxy)methoxycarbonyl chloride, (pivaloyloxy)methoxycarbonyl chloride, (isobutanoyloxy)methoxycarbonyl chloride, (nicotynyloxy) methoxycarbonyl chloride, 1-(acetoxy)ethoxycarbonyl chloride, 1-(pivaloyloxy)ethoxycarbonyl chloride, 1-(isobutanoyloxy)ethoxycarbonyl chloride, and 1-(nicotinyloxy)ethoxycarbonyl chloride; and substituted alkyl 4-nitrophenyl carbonates such as (acetoxy)methyl 4-nitrophenyl carbonate, (pivaloyloxy)methyl 4-nitrophenyl carbonate, (isobutanoyloxy)methyl 4-nitrophenyl carbonate, (nicotinyloxy)methyl 4-nitrophenyl carbonate, 1-(acetoxy) ethyl 4-nitrophenyl carbonate, (pivaloyloxy)ethyl 4-nitrophenyl carbonate, 1-(isobutanoyloxy)ethyl 4-nitrophenyl carbonate, and 1-(nicotinyloxy)ethyl 4-nitrophenyl carbonate. The carbonic acid derivative may be produced, for example, by the method of M. Folkmann et al. (Synthesis, 1159 (1990)).

Typical "bases" include organic bases such as trimethylamine, triethylamine, N-methylmorpholine, pyridine and imidazole; and inorganic bases such as sodium hydroxide, sodium carbonate, sodium bicarbonate, potassium hydroxide, potassium carbonate, potassium bicarbonate, magnesium hydroxide, magnesium carbonate, and magnesium bicarbonate.

The reaction is generally conducted in the absence of a solvent, or in the presence of such solvent as acetnitrile, dioxane, ethyl acetate, tetrahydrofuran, ether, acetone, N,N-dimethylformamide, chloroform, methylene chloride, ethylene chloride, hexane, dimethylsulphoxide, hexamethylphosphoric triamide, pyridine, methanol, ethanol, isopropanol, water, and acetic acid, which may be used either alone or in combination of two or more.

A further method for synthesizing the compound of formula 1 when M in formula 2 represents a (C: 1–10) alkyl comprises the step of reacting the compound of formula 1 wherein M in formula 2 is hydrogen with an alkylhalide optionally in the presence of a base. The synthesis may be completed also by reacting the compound with an aldehyde to synthesize an imine, followed by reduction of the imine; or by reacting the compound with an aldehyde under reductive conditions.

Typical "alkyl halides" include methyl chloride, methyl bromide, methyl iodide, ethyl chloride, ethyl bromide, ethyl iodide, propyl chloride, propyl bromide, propyl iodide, isopropyl chloride, isopropyl bromide, isopropyl iodide, butyl chloride, butyl bromide, butyl iodide, isobutyl chloride, isobutyl bromide, and isobutyl iodide.

Typical "aldehydes" include formaldehyde, acetaldehyde, and propionaldehyde.

Typical "bases" include organic bases such as trimethylamine, triethylamine, N-methylmorpholine and imidazole; and inorganic bases such as sodium hydroxide, sodium carbonate, sodium bicarbonate, potassium hydroxide, potassium carbonate, potassium bicarbonate, magnesium hydroxide, magnesium carbonate, and magnesium bicarbonate.

"Reductive conditions" designate such conditions as catalytic reductive conditions wherein a metal catalyst such as palladium, nickel, platinum, or rhodium is employed; reductive conditions wherein a metal hydride such as sodium boron hydride, lithium boron hydride, lithium aluminum hydride or diisobutylaluminum hydride is employed; and reductive conditions wherein a metal such as lithium or sodium is employed.

(3)

In formula 3, A and B are as defined for formula 1.

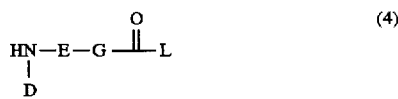

(4)

In formula 4, D, E, G and L are as defined for formula 1.

The compound of formula 3 may be produced by condensing the compound of the formula 5 as will be shown below and the compound of the formula 6 as will be shown below using a base in the optional presence of a catalyst to obtain the compound of formula 7; and subsequently, hydrolyzing the compound with optional use of an acid or a base, or eliminating the protecting group through reduction with hydrogen or the like.

Typical "bases" include organic bases such as triethylamine, trimethylamine, N-methylmorpholine, pyridine and imidazole; and inorganic bases such as sodium hydroxide, sodium carbonate, sodium bicarbonate, potassium hydroxide, potassium carbonate, potassium bicarbonate, magnesium hydroxide, magnesium carbonate, and magnesium bicarbonate.

The reaction is generally conducted in the absence of a solvent, or in the presence of such solvent as acetnitrile, dioxane, ethyl acetate, tetrahydrofuran, ether, acetone, N,N-dimethylformamide, chloroform, methylene chloride, ethylene chloride, hexane, toluene, benzene, dimethylsulphoxide, hexamethylphosphoric triamide, pyridine, methanol, ethanol, isopropanol, water, and acetic acid, which may be used either alone or in combination of two or more.

The "protecting group" is a group which may be substituted to hydrogen by an appropriate reaction when U in formula 7 is a substituent other than hydrogen, and which may typically be a known protecting group such as methoxy, ethoxy, benzyloxy, p-nitrobenzyloxy, t-butoxy, cyclohexyloxy, or the like.

The reaction conditions for the "cleavage of the protecting group" may be selected in accordance with the type of the protecting group, for example, from acid treatment by hydrogen chloride, hydrogen bromide, hydrogen fluoride, methanesulfonic acid, or a mixture thereof; base treatment by lithium hydroxide, sodium hydroxide, potassium hydroxide, barium hydroxide, sodium carbonate, potassium carbonate, sodium bicarbonate, potassium bicarbonate, hydrazine, diethylamine, piperidine, or the like; reduction treatment using a metal catalyst such as palladium-carbon; and the like. The reaction is generally conducted in the absence of a solvent, or in the presence of such solvent as acetnitrile, dioxane, ethyl acetate, tetrahydrofuran, ether, acetone, N,N-dimethylformamide, chloroform, methylene chloride, ethylene chloride, hexane, methanol, ethanol, isopropanol, water, and acetic acid, which may be used either alone or in combination of two or more.

A typical production example of the compound of formula 5 is 1-(benzyloxycarbonyl)-4-hydroxypiperidine (H. C. Brown et al., Journal of Organic Chemistry, vol. 50, 1582–9 (1985)). An exemplary method for condensing the compound of formula 5 with the compound of formula 6 is the method of H. H. Friedman (Tetrahedron Letters No.38, 3251 (1975)) when T in the compound of formula 6 is bromine.

(5)

In formula 5, A is as defined for formula 2.

(6)

In formula 6, B is as defined for formula 1; T is a halogeno, an alkylsulfonate, or an arylsulfonate; U is hydroxy, a (C: 0–10) alkylamino, a (C: 1–10) alkoxy, or an aryl (C: 0–8) alkoxy; and C is carbon.

(7)

In formula 7, A, B and U are as defined for formula 1, and U is as defined in formula 6.

The compound of formula 4 may be produced by condensing amine at second position of the 1,2,3,4-tetrahydroisoquinoline derivative of formula 8 as will be shown below and the compound of the formula 9 by optional use of a base or the like to obtain the compound of formula 10; and reducing the compound of formula 10 when V in formula 10 is nitro, or alternatively, eliminating the amino-protecting group if V in formula 10 is not nitro. Alternatively, when G is an optionally substituted alkylene containing two carbon atoms, the compound of formula 4 may be produced by condensing amine at second position of the 1,2,3,4-tetrahydroisoquinoline derivative of formula 8 as will be shown below and the compound of the formula 11 by optional use of a base or the like to obtain the compound of formula 10; and reducing the compound of formula 10 when V in formula 10 is nitro, or alternatively, eliminating the amino-protecting group if V in formula 10 is not nitro.

Typical "bases" include organic bases such as triethylamine, trimethylamine, N-methylmorpholine, and imidazole; and inorganic bases such as sodium hydroxide, sodium carbonate, sodium bicarbonate, potassium hydroxide, potassium carbonate, potassium bicarbonate, magnesium hydroxide, magnesium carbonate, and magnesium bicarbonate.

The "reduction" of the "nitro group" may be effected by catalytic reduction in the presence of a metal catalyst, for example, a palladium catalyst such as palladium black, palladium-carbon, or palladium-barium sulfate; a nickel catalyst such as Raney nickel or reduction nickel; an iron catalyst such as reduction iron or Raney iron; a rhodium catalyst such as rhodium-alumina; a platinum catalyst such as platinum black, platinum sulfate-carbon, platinum oxide, or platinum plate; a cobalt catalyst such as reduction cobalt or Raney cobalt; a copper catalyst such as reduction copper, Ullmann copper or Raney copper; or the like; or by reduction in the presence of cyclohexadiene, cyclohexene, or the like. The reduction may also be effected under acidic or neutral conditions in the presence of zinc, iron, tin, or tin oxide; or by using a sulfate such as sodium sulfate, sodium hydrosulfide, sodium dithionite, or ammonium sulfate, or a metal hydride such as sodium boron hydride in the co-presence of lithium aluminum hydride or copper chloride.

The reaction conditions for the "cleavage of the amino-protecting group" may be selected in accordance with the type of the protecting group, for example, from acid treatment by hydrogen chloride, hydrogen bromide, hydrogen fluoride, methanesulfonic acid, or a mixture thereof; base treatment by lithium hydroxide, sodium hydroxide, potassium hydroxide, barium hydroxide, sodium carbonate, potassium carbonate, sodium bicarbonate, potassium bicarbonate, hydrazine, diethylamine, piperidine, or the like; reduction treatment using a metal catalyst such as palladium-carbon; and the like.

The reaction is generally conducted in the absence of a solvent, or in the presence of such solvent as acetnitrile, dioxane, ethyl acetate, tetrahydrofuran, ether, acetone, N,N-dimethylformamide, chloroform, methylene chloride, ethylene chloride, hexane, toluene, benzene, methanol, ethanol, isopropanol, water, acetic acid, hydrochloric acid, and aqueous ammonia, which may be used either alone or in combination of two or more.

Typical production examples of the compound of formula 8 include 7-nitro-1,2,3,4-tetrahydroisoquinoline (Ajao, J. F. et al., Journal of Heterocyclic Chemistry, vol.22, 329–31 (1985)) and 7-nitro-1-phenyl-1,2,3,4-tetrahydroisoquinoline (Paul, R. et al., Journal of Medicinal Chemistry, vol. 15, 720–6 (1972)).

(8)

In formula 8, E is as defined for formula 1; V represents nitro or a protected amino such as a ((C: 1–10) alkoxycarbonyl)amino, an (aryl (C: 0–8) alkoxycarbonyl) amino, a (C: 1–10) alkylamide, succinylimide or phthaloylimide; and C represents carbon.

(9)

In formula 9, G and L are as defined for formula 1; T is a halogeno, an alkylsulfonate, or an arylsulfonate.

(10)

In formula 10, E, G and L are as defined for formula 1, and V is as defined for formula 8.

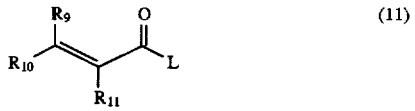

(11)

In formula 11, L is as defined for formula 1; and $R_9$, $R_{10}$ and $R_{11}$ are independently hydrogen, a (C: 1–10) alkyl, an aryl (C: 0–8) alkyl, or a halogeno; and C is carbon.

The tetrahydroisoquinoline derivative of the present invention is used as an antagonist for GPIIb/IIIa receptor or an agent for preventing the formation of thrombus by the binding to the GPIIb/IIIa receptor of an adhesive protein such as fibrinogen, namely, as a platelet agglutination-inhibitory agent or an antithrombotic agent. The compound of the present invention is used for treating and for preventing the recurrence of myocardial infarction, unstable stenocardia, temporary brain ischemic stroke, or peripheral artery obstruction, which are diseases wherein the thrombus formation is involved as a factor. The tetrahydroisoquinoline derivative of the present invention is also effective in preventing the activation of platelets induced by interaction of the platelets with an artificial surface upon extracorporeal blood circulation in the use of an oxygenator or in the case of dialysis. The tetrahydroisoquinoline derivative of the present invention is also useful in coronary bypass formation, reconstruction of blood circulation in the obstruction of peripheral artery, and prevention of graft blockage in provision of a dialysis shunt.

The dose, which may be determined according to the symptom, is generally in the range of from 0.10 to 600 mg/day, and preferably, from 1 to 200 mg/day in the case of an adult, and this dose may be administered in one to three administrations. The agent may be administered by any adequate route, and oral administration is particularly desirable. The agent, however, may be administered intravenously, or by direct injection into the lesion by means of a syringe or a catheter.

The compound of the present invention may be formed into any dosage form adequate for administration as the only effective component or as one of the effective components either alone or with a pharmaceutical carrier. Exemplary dosage forms include, tablet, powder, capsule, granule, syrup, solution, suspension, injection, eye drop, and suppository.

Exemplary pharmaceutical carriers include excipients such as starch, sucrose, lactose, methylcellulose, carboxymethyl cellulose, crystalline cellulose, sodium arginate, calcium hydrogen phosphate, magnesium metasilicate aluminate, anhydrous silicic acid, and synthetic aluminum silicate; binders such as hydroxypropylcellulose, hydroxypropylmethylcellulose, gelatin, and polyvinylpyrrolidone; disintegrants such as calcium carboxymethyl cellulose, cross-linked sodium carboxymethyl cellulose and cross-linked polyvinylpyrrolidone; lubricants such as magnesium stearate and talk; coating agent such as cellulose acetate phthalate, hydroxypropylmethylcellulose acetate succinate, methacrylic acid and methyl methacrylate copolymer; dissolution aids such as polyethylene glycol; emulsifying agents such as sodium laurylsulfate, lecithin, sorbitan monooleate, polyoxyethylene cetyl ether, sucrose fatty acid ester, polyoxyethylene-cured caster oil and glyceryl monostearate; chelating agent such as EDTA; buffers; emolients; preservatives; and bases such as cacao fat and Witepsole W35.

BEST MODE FOR CARRYING OUT THE INVENTION

The present invention is described in further detail by referring to Examples and Experiments, which by no means limit the scope of the invention.

(EXAMPLE 1)

(1-1)

1.5 g of 7-nitro-1,2,3,4-tetrahydroisoquinoline hydrochloride was dissolved in 20 ml of ethanol, and 2.9 g of sodium hydrogencarbonate, 2.3 g of ethyl bromoacetate, and a catalytic amount of potassium iodide were added to the solution. The resulting solution was heated and stirred overnight under reflux. The resulting solution was extracted with ethyl acetate, washed with the water and saturated aqueous solution of sodium chloride, and then dried with anhydrous sodium sulfate. After separating the desiccant by filtration, the filtrate was purified by silica gel column chromatography to obtain 1.1 g of 2-(ethoxycarbonylmethyl)-7-nitro-1,2,3,4-tetrahydroisoquinoline (yield: 57%, oily product).

(1-2)

1.1 g of 2-(ethoxycarbonylmethyl)-7-nitro-1,2,3,4-tetrahydroisoquinoline was dissolved in 20 ml of ethanol, and a catalytic amount of 10% palladium-carbon was added to the solution. The solution was stirred overnight in hydrogen atmosphere. The catalyst was separated by filtration and the solvent was distilled off under reduced pressure to obtain 0.88 g of 7-amino-2-(ethoxycarbonylmethyl)-1,2,3,4-tetrahydroisoquinoline, which was an oily product. This product with no further purification was dissolved in 10 ml of N,N-dimethylformamide (DMF), and 1.3 g of 1-(benzyloxy-carbonyl)-4-(carboxymethoxy)piperidine and 1.1 g of 1-ethyl-3-(3-dimethylaminopropyl)carbodiimide which have been separately synthesized were added to the solution. After adding water, the solution was extracted with ethyl acetate, washed with saturated aqueous solution of sodium hydrogencarbonate and saturated aqueous solution of sodium chloride in this order, and dried with anhydrous sodium sulfate. After separating the desiccant by filtration, the product was purified by silica gel column chromatography to obtain 1.7 g of 7-[1-(benzyloxycarbonyl)piperidine-4-yloxyacetylamino]-2-(ethoxycarbonylmethyl)- 1,2,3,4-tetrahydroisoquinoline. (Yield: 90%, oily product).

(1-3)

1.2 g of 7-[1-(benzyloxycarbonyl)piperidine-4-yloxyacetylamino]-2-(ethoxycarbonylmethyl)-1,2,3,4-tetrahydroisoquinoline was dissolved in 10 ml of ethanol, and 3 ml of 2N aqueous solution of sodium hydroxide was added to the solution. The solution was stirred overnight at room temperature. Dilute hydrochloric acid was added dropwise to the resulting solution to acidify the solution, and the solution was concentrated under reduced pressure, and dissolved in anhydrous ethanol. The insoluble content was separated by filtration, and the solvent was distilled off. The product was dissolved in 5 ml of 25% hydrogen bromide-acetic acid, and allowed to stand at room temperature for 30 minutes. Concentration at reduced pressure was carried out to produce 7-(piperidine-4-yloxyacetylamino)-2-carboxymethyl-1,2,3,4-tetrahydroisoquinoline (yield: constant; amorphous solid with no color). Instrumental analysis data of this product support the structural formula of formula 12, below.

$^1$H-NMR (CD$_3$OD) δ(ppm): 7.35–7.20 (m, 2H), 7.08 (d, 1H, J=6 Hz), 4.10 (s, 2H), 3.75 (s, 2H), 3.70–3.62 (m, 1H), 3.30–3.18 (m, 6H), 3.00–2.82 (m, 4H), 2.15–1.78 (m, 4H)

(12)

(EXAMPLE 2)

(2-1)

1.5 g of 7-nitro-1,2,3,4-tetrahydroisoquinoline hydrochloride was dissolved in 20 ml of ethanol, and 2.9 g of sodium hydrogencarbonate, 2.3 g of ethyl bromopropionate, and a catalytic amount of potassium iodide were added to the solution. The resulting solution was heated and stirred overnight under reflux. The resulting solution was extracted with ethyl acetate, washed with water and saturated aqueous solution of sodium chloride, and then dried with anhydrous sodium sulfate. After separating the desiccant by filtration, the product was purified by silica gel column chromatography to obtain 1.1 g of 2-(2-(ethoxycarbonyl)ethyl)-7-nitro-1,2,3,4-tetrahydroisoquinoline (yield: 57%, oily product).

(2-2)

1.1 g of 2-(2-(ethoxycarbonyl)ethyl)-7-nitro-1,2,3,4-tetrahydroisoquinoline was dissolved in 20 ml of ethanol, and a catalytic amount of 10% palladium-carbon was added to the solution. The solution was stirred overnight in hydrogen atmosphere. The catalyst was separated by filtration and the solvent was distilled off under reduced pressure to obtain 0.88 g of 7-amino-2-(2-(ethoxycarbonyl)ethyl)-1,2,3,4-tetrahydroisoquinoline, which was an oily product. This product with no further purification was dissolved in 10 ml of DMF, and 1.3 g of 1-(benzyloxycarbonyl)-4-(carboxymethoxy)piperidine and 1.1 g of 1-ethyl-3-(3-dimethylaminopropyl)carbodiimide which have been separately synthesized were added to the solution. After adding water, the solution was extracted with ethyl acetate, washed with saturated aqueous solution of sodium hydrogencarbonate and saturated aqueous solution of sodium chloride in this order, and dried with anhydrous sodium sulfate. After separating the desiccant by filtration, the product was purified by silica gel column chromatography to obtain 1.7 g of 7-[1-(benzyloxycarbonyl)piperidine-4-yloxyacetylamino]-2-(2-(ethoxycarbonyl)ethyl)-1,2,3,4-tetrahydroisoquinoline (yield: 90%, oily product).

(2-3)

1.2 g of 7-[1-(benzyloxycarbonyl)piperidine-4-yloxyacetylamino]-2-[2-(ethoxycarbonyl)ethyl]-1,2,3,4-tetrahydroisoquinoline was dissolved in 10 ml of ethanol, and 3 ml of 2N aqueous solution of sodium hydroxide was added to the solution. The solution was stirred overnight at room temperature. Dilute hydrochloric acid was added dropwise to the resulting solution to acidify the solution, and the solution was concentrated under reduced pressure, and dissolved in anhydrous ethanol. The insoluble content was separated by filtration, and the solvent was distilled off. The product was dissolved in 5 ml of 25% hydrogen bromide-acetic acid, and allowed to stand at room temperature for 30 minutes. Concentration at reduced pressure was carried out to produce 7-(piperidine-4-yloxyacetylamino)-2-carboxyethyl-1,2,3,4-tetrahydroisoquinoline (yield: constant; amorphous solid with no color). Instrumental analysis data of this product support the structural formula of formula 13, below.

$^1$H-NMR (CD$_3$OD) δ(ppm): 7.55 (s, 1H), 7.50 (d, 1H, J=6 Hz), 7.22 (d, 1H, J=6 Hz), 4.12 (s, 2H), 3.85–3.78 (m, 8H), 3.75 (s, 2H), 3.60–3.28 (m, 8H), 3.20–2.95 (m, 4H), 2.35–1.92 (m, 4H)

(13)

(EXAMPLE 3)

The procedure of Example 1 was repeated except that ethyl bromoacetate was replaced with ethyl 4-bromobutanoate to obtain 7-(piperidine-4-yloxyacetylamino)-2-(3-carboxypropyl)-1,2,3,4-tetrahydroisoquinoline (amorphous solid). Instrumental analysis data of this product support the structural formula of formula 14, below.

$^1$H-NMR (CD$_3$OD) δ(ppm): 7.52 (s, 1H), 7.40 (d, 1H, J=6 Hz), 7.30 (d, 1H, J=6 Hz), 4.12 (s, 2H), 3.80–3.68 (m, 3H), 3.52–3.15 (m, 8H), 3.22–2.98 (m, 4H), 2.12–1.80 (m, 6H)

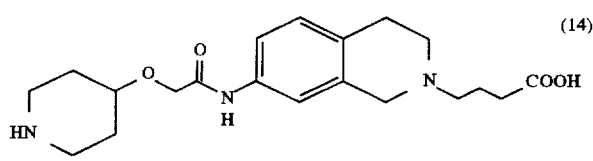

(14)

(EXAMPLE 4-1)

1.1 g of 7-|1-(benzyloxycarbonyl)piperidine-4-yloxyacetylamino|-2-(2-(ethoxycarbonyl)ethyl)-1,2,3,4-tetrahydroisoquinoline, which is an intermediate product of Example 2 was dissolved in 20 ml of ethanol. A catalytic amount of 10% palladium-carbon was added to the solution, and the solution was stirred overnight under hydrogen atmosphere. The catalyst was separated by filtration, and the solvent was distilled off under reduced pressure. The product was purified by silica gel column chromatography to obtain 0.46 g of 7-(piperidine-4-yloxyacetylamino)-2-(2-(ethoxycarbonyl)ethyl)-1,2,3,4-tetrahydroisoquinoline (yield: 53%, oily product). Instrumental analysis data of this product support the structural formula of formula 15, below.

$^1$H-NMR (CD$_3$OD) δ(ppm): 8.30 (s, 1H), 7.35 (s, 1H), 7.25 (d, 1H, J=6 Hz), 7.02 (d, 1H, J=6 Hz), 4.12 (q, 2H, J=7 Hz), 4.05 (s, 2H), 3.62 (s, 2H), 3.55–3.45 (m, 1H), 3.15–3.05 (m, 2H), 2.90–2.78 (m, 4H), 2.75 (d, 2H, J=7 Hz), 2.62–2.52 (m, 4H), 2.00–1.92 (m, 2H), 1.90–1.78 (br, 1H), 1.58–1.45 (m, 2H), 1.22 (t, 3H, J=7 Hz)

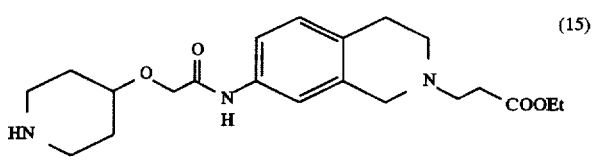

(15)

(EXAMPLE 4-2)

(4-2-1)

To 125 ml of suspension in ethanol of 136 g of 7-nitro-1,2,3,4-tetrahydroisoquinoline hydrochloride was added 98 ml of triethylamine and 83 ml of ethyl acrylate, and the solution was heated and stirred overnight under reflux. The solution was concentrated under reduced pressure, and the residue was extracted with ethyl acetate, washed with water, and dried with anhydrous sodium sulfate. After separating the desiccant by filtration, the filtrate was concentrated under reduced pressure to obtain 2-(2-(ethoxycarbonyl)ethyl)-7-nitro-1,2,3,4-tetrahydroisoquinoline. The thus obtained 2-(2-(ethoxycarbonyl)ethyl)-7-nitro-1,2,3,4-tetrahydroisoquinoline was dissolved in 1,000 ml of ethanol, and a catalytic amount of 10% palladium-carbon was added to the solution. The solution was stirred overnight under hydrogen atmosphere. The catalyst was separated by filtration, and the filtrate was concentrated under reduced pressure to obtain 7-amino-2-(2-(ethoxycarbonyl)ethyl)-1,2,3,4-tetrahydroisoquinoline, which was a solid.

To 1,200 ml of methylene chloride solution of 186 g of 1-(benzyloxycarbonyl)-4-(carboxymethoxy)piperidine and 105 ml of triethylamine, which had been cooled to −15° C., was added dropwise 66 ml of ethyl chlorocarbonate, and then 300 ml of methylene chloride solution of 7-amino-2-(2-(ethoxycarbonyl)ethyl)-1,2,3,4-tetrahydroisoquinoline. The solution was stirred in an ice bath for 1 hour, and methylene chloride was distilled off under reduced pressure. The solution was extracted with ethyl acetate, washed with water, saturated aqueous solution of sodium hydrogencarbonate and saturated aqueous solution of sodium chloride in this order, and dried with anhydrous sodium sulfate. After separating the desiccant by filtration, the product was concentrated under reduced pressure, and ether was added to the residue to obtain 237 g of 7-[1-(benzyloxycarbonyl)piperidine-4-yloxyacetylamino|-2-(2-(ethoxycarbonyl)ethyl)-1,2,3,4-tetrahydroisoquinoline (yield: 71%, crystal with no color).

(4-2-2)

237 g of 7-[1-(benzyloxycarbonyl)piperidine-4-yloxyacetylamino|-2-(2-(ethoxycarbonyl)ethyl)-1,2,3,4-tetrahydroisoquinoline was dissolved in 1,800 ml of dioxane, and a catalytic amount of 10% palladium-carbon was added to the solution. The solution was stirred overnight in hydrogen atmosphere. The catalyst was separated by filtration and the solvent was distilled off under reduced pressure. The residue was dissolved in 2,500 ml of ethanol, and 176 g of tosyl acid monohydrate was added to the solution. The crystals formed were collected by filtration to obtain 320 g of 7-(piperidine-4-yloxyacetylamino)-2-(2-ethoxycarbonyl)ethyl)-1,2,3,4-tetrahydroisoquinoline 2 tosylate (yield: 96%; crystals with no color). Instrumental analysis data of this product support the structural formula of formula 16, below. melting point: 204°–206° C.

$^1$H-NMR (D$_2$O) δ(ppm): 7.80 (d, 4H, J=8.0 Hz), 7.35 (d, 4H, J=8.0 Hz), 7.38–7.26 (m, 3H), 4.48–4.40 (brS, 2H), 4.26 (s, 2H), 4.24 (q, 2H, J=6.8 Hz), 3.91–3.84 (m, 1H), 3.65–3.58 (m, 4H), 3.48–3.40 (m, 2H), 3.22–3.20 (m, 4H), 3.01 (t, 2H, J=6.8 Hz), 2.39 (s, 6H), 2.22–2.13 (m, 2H), 2.05–1.90 (m, 2H), 1.29 (t, 3H, J=7.2 Hz)

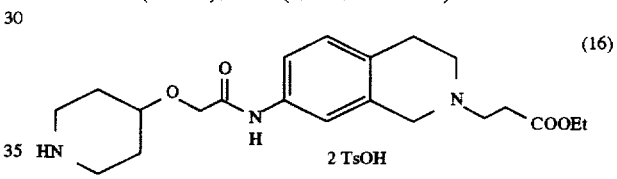

(16)

(EXAMPLE 4-3)

The procedure of Example 4-2-2 was repeated except that tosyl acid monohydrate was replaced with maleic acid to obtain 7-(piperidine-4-yloxyacetylamino)-2-(2-(ethoxycarbonyl)ethyl)-1,2,3,4-tetrahydroisoquinoline maleate (crystals with no color). Instrumental analysis data of this product support the structural formula of formula 17, below. melting point: 185° C.

$^1$H-NMR (D$_2$O) δ(ppm): 7.34–7.26 (m, 3H), 6.24 (s, 2H), 4.58–4.36 (brS, 2H), 4.25 (s, 2H), 4.20 (q, 2H, J=7.2 Hz), 3.90–3.84 (m, 1H), 3.65–3.58 (m, 4H), 3.46–3.38 (m, 2H), 3.21–3.10 (m, 4H), 2.99 (t, 2H, J=6.8 Hz), 2.21–2.12 (m, 2H), 1.98–1.88 (m, 2H), 1.26 (t, 3H, J=7.2 Hz)

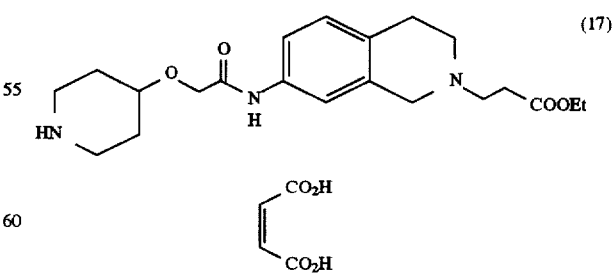

(17)

EXAMPLE (4-4)

The procedure of Example 4-2-2 was repeated except that tosyl acid monohydrate was replaced with mesyl acid to obtain 7-(piperidine-4-yloxyacetylamino)-2-(2-(ethoxycarbonyl)ethyl)- 1,2,3,4-tetrahydroisoquinoline 2 mesylate (crystals with no color). Instrumental analysis data of this product support the structural formula of formula 18, below. melting point: 139°–140° C.

$^1$H-NMR (D$_2$O) δ(ppm): 7.35 (s, 3H), 4.60–4.38 (brS, 2H), 4.26 (s, 2H), 4.21 (q, 2H, J=7.6 Hz), 3.92–3.84 (m, 1H), 3.62 (t, 2H, J=7.2 Hz), 3.46–3.38 (m, 2H), 3.22–3.11 (m, 4H), 3.00 (t, 2H, J=7.2 Hz), 2.78 (s, 6H), 2.21–2.12 (m, 2H), 1.98–1.88 (m, 2H), 1.26 (t, 3H, J=7.6 Hz)

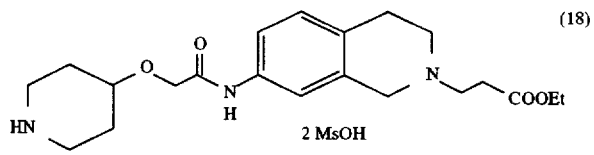

(18)

2 MsOH (EXAMPLE 5)

(5-1)
66 mg of sodium hydride (60%) was suspended in 10 ml of THF, and to this suspension was added a solution of 0.71 g of 7-[1-(benzyloxycarbonyl)piperidine-4-yloxyacetylamino]-2-[2-(ethoxycarbonyl)ethyl]-1,2,3,4-tetrahydroisoquinoline, which is an intermediate product of Example 2 in 10 ml of THF in an ice bath. After stirring for 30 minutes, 0.13 ml of methyl iodide was added to the solution, and the solution was stirred at room temperature for 3 hours. The resulting solution was extracted with ethyl acetate, washed with water and saturated aqueous solution of sodium chloride, and dried with anhydrous sodium sulfate. After separating the desiccant by filtration, the filtrate was purified by silica gel column chromatography to obtain 0.50 g of 7-{[1-(benzyloxycarbonyl)piperidine-4-yloxyacetyl]methylamino}-2-[2-(ethoxycarbonyl)ethyl]-1,2,3,4-tetrahydroisoquinoline (yield: 68%; oily product).

(5-2)
7-{[1-(benzyloxycarbonyl)piperidine-4-yloxy-acetyl]methylamino}-2-[2-(ethoxycarbonyl)ethyl]-1,2,3,4-tetrahydroisoquinoline was deblocked by repeating the procedure of Example 1 to obtain 7-[(piperidine-4-yloxyacetyl)methylamino]-2-[2-(carboxy)ethyl]-1,2,3,4-tetrahydroisoquinoline (amorphous solid). Instrumental analysis data of this product support the structural formula of formula 19, below.

$^1$H-NMR (CD$_3$OD) δ(ppm): 7.53 (s, 1H), 7.42 (d, 1H, J=6 Hz), 7.22 (d, 1H, J=6 Hz), 3.85 (s, 2H), 3.75–3.68 (m, 3H), 3.60–3.28 (m, 8H), 3.22 (s, 3H), 3.20–2.92 (m, 4H), 2.30–1.90 (m, 4H)

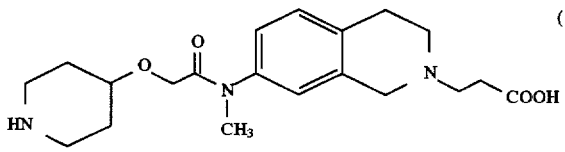

(19)

(EXAMPLE 6)

The procedure of Example 2 was repeated except that 7-nitro-1,2,3,4-tetrahydroisoquinoline hydrochloride was replaced with 7-nitro-1-phenyl-1,2,3,4-tetrahydroisoquinoline to obtain 2-(carbonylethyl)-1-phenyl-7-(piperidine-4-yloxyacetylamino)-1,2,3,4-tetrahydroisoquinoline (amorphous solid). Instrumental analysis data of this product support the structural formula of formula 20, below.

$^1$H-NMR (CD$_3$OD) δ(ppm): 7.62 (d, 1H, J=6 Hz), 7.55–7.38 (mB, 5H), 7.32 (d, 1H, J=6 Hz), 7.20 (s, 1H), 5.95 (s, 1H), 4.10 (s, 2H), 3.80–3.65 (m, 2H), 3.62–3.20 (m, 7H), 3.15–2.90 (m, 4H), 2.10–1.90 (m, 4H)

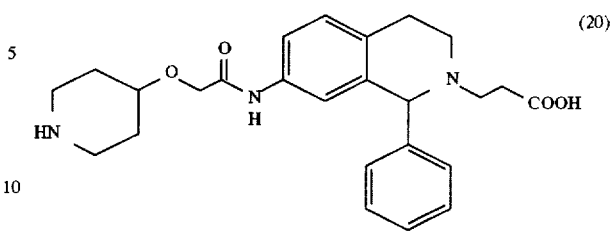

(20)

(EXAMPLE 7)

(7-1)
3.05 g of 2, 6-dimethyl-4-hydroxypiperidine hydrochloride obtained by catalytic reduction with rhodium alumina of the solution of 2.56 g of 2,6-dimethyl-4-hydroxypiperidine in hydrochloric acid solution was dissolved in 20 ml of water, and 19 ml of 2N aqueous solution of sodium hydroxide was added to the solution in an ice bath. To this solution was added dropwise 40 ml of THF and 2.7 ml of benzyloxycarbonyl chloride in this order, and the solution was stirred at room temperature for 2 hours. The residue was extracted with ethyl acetate, washed with saturated aqueous solution of sodium chloride, and dried with anhydrous sodium sulfate. After separating the desiccant by filtration, the filtrate was concentrated under reduced pressure, and the resulting residue was purified by silica gel column chromatography. From the fractions eluted with chloroform-methanol (10:1 v/v) was obtained 1.91 g of N-benzyloxycarbonyl-2,6-dimethyl-4-hydroxypiperidine, which was an oily product with no color (yield: 39%).

(7-2)
To 10 ml of toluene was dissolved 1.91 g of N-benzyloxycarbonyl-2,6-dimethyl-4-hydroxypiperidine, and to this solution were added 1.70 g of tert-butyl bromoacetate, 0.08 g of tetrabutylammonium sulfate and 1 ml of water, and then aqueous solution of sodium hydroxide in an ice bath. The solution was stirred overnight at room temperature, washed with water and saturated aqueous solution of sodium chloride, and dried with anhydrous sodium sulfate. After separating the desiccant by filtration, the filtrate was concentrated under reduced pressure, and the resulting residue was purified by silica gel column chromatography. From the fractions eluted with chloroform-methanol (100:1 v/v) was obtained 1.11 g of N-benzyloxycarbonyl-4-tert-butoxycarbonylmethyloxy-2, 6-dimethylpiperidine, which was an oily product (yield: 41%).

(7-3)
1.11 g of N-benzyloxycarbonyl-4-tert-butoxycarbonylmethyloxy-2,6-dimethylpiperidine was dissolved in 5 ml of methylene chloride, and 2 ml of trifluoroacetic acid was added. The solution was stirred overnight at room temperature, and the resulting solution was concentrated under reduced pressure. The filtrate was concentrated under reduced pressure, and the resulting residue was purified by silica gel column chromatography. From the fractions eluted with chloroform-methanol (9:1 v/v) was obtained 0.61 g of N-benzyloxycarbonyl-4-carboxymethyloxy-2,6-dimethylpiperidine, which was an oily product with no color (yield: 65%).

(7-4)
0.61 g of N-benzyloxycarbonyl-4-carboxymethyloxy-2,6-dimethylpiperidine was dissolved in 15 ml of DMF, and to this solution was added 0.88 g of BOP reagent, 0.45 g of 7-amino-2-(2-(ethoxycarbonyl)ethyl)-1,2,3,4- tetrahydroisoquinoline obtained in Example 2, and 0.80 ml of triethylamine in an ice bath, and the solution was stirred overnight at room temperature. The resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the filtrate was concentrated under reduced pressure, and the residue was purified by silica gel column chromatography. From the fractions eluted with chloroform-methanol (100:1 v/v) was obtained 0.74 g of 7-[1-(benzyloxycarbonyl)-2,6-dimethylpiperidine-4-yloxylacetylamino]-2-[2-(ethoxycarbonyl)ethyl]-1,2,3,4-tetrahydroisoquinoline, which was an oily product (yield: 71%).

(7-5)

0.53 g of 7-[1-(benzyloxycarbonyl)-2,6-dimethylpiperidine-4-yloxyacetylamino]-2-[2-(ethoxycarbonyl) ethyl]-1,2,3,4-tetrahydroisoquinoline was dissolved in 10 ml of methanol, and to this solution was added 0.28 g of potassium carbonate and 1 ml of water, and the solution was stirred under reflux at an elevated temperature for 1 hour. The resulting solution was acidified by adding dilute hydrochloric acid, concentrated under reduced pressure, and dissolved in anhydrous ethanol. The insoluble contents were separated by filtration, and the filtrate was concentrated to obtain 0.58 g of 7-[1-(benzyloxycarbonyl)-2,6-dimethylpiperidine-4-yloxyacetylamino]-2-(2-carboxyethyl)-1,2,3,4-tetrahydroisoquinoline, which was an amorphous solid with no color (yield: 100%).

(7-6)

0.21 g of 7-[1-(benzyloxycarbonyl)-2,6-dimethylpiperidine-4-yloxyacetylamino]-2-(2-carboxyethyl)-1,2,3,4-tetrahydroisoquinoline was dissolved in 5 ml of ethanol, and to this solution was added a catalytic amount of 10% palladium-carbon. The solution was stirred overnight in hydrogen atmosphere. After separating the catalyst by filtration, the filtrate was concentrated under reduced pressure to obtain 7-(2,6-dimethylpiperidine-4-yloxyacetylamino)-2-(2-carboxyethyl)-1,2,3,4-tetrahydroisoquinoline, which was an amorphous solid with no color. Instrumental analysis data of this product support the structural formula of formula 21, below.

$^1$H-NMR (CD$_3$OD) δ(ppm): 7.20 (s, 1H), 7.20 (d, 2H), 7.15 (d, 2H), 4.18 (s, 2H), 4.02 (s, 2H), 3.75–3.63 (m, 1H), 3.65–2.98 (m, 8H), 2.55 (t, 2H), 2.40–2.10 (m, 2H), 1.43–1.30 (m, 8H)

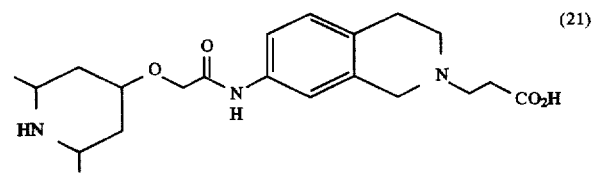

(21)

(EXAMPLE 8)

(8-1)

To a suspension (160 ml) of 3.2 g of sodium hydride in tetrahydrofuran (THF) was added a solution (15 ml) of 15.0 g of 1-benzyl-4-piperidone in THF in an ice bath, and the solution was stirred at room temperature for 30 minutes. 5.92 ml of methyl iodide was added to this solution, and the solution was stirred at 60° C. for 4 hours. The salt precipitated was separated by filtration, and after concentrating the filtrate under reduced pressure, water was added to the concentrate. The solution was extracted with ethyl acetate, and the organic layer was washed with saturated aqueous solution of sodium chloride, dried with anhydrous sodium sulfate, and concentrated under reduced pressure. The residue was purified by silica gel column chromatography, and from the fractions eluted with ethyl acetate-hexane (1:1 v/v) was obtained 3.98 g of 1-benzyl-3-methyl-4-piperidone (yield: 25%).

(8-2)

A solution (15 ml) of 3.98 g of 1-benzyl-3-methyl-4-piperidone in diethyl ether was added to a suspension (10 ml) of 0.78 g of aluminum lithium hydride in diethyl ether in an ice bath, and the solution was heated under reflux for 3 hours. Water was added to the solution, and the solution was extracted with ethyl acetate, and the organic layer was washed with saturated aqueous solution of hydrogen chloride. The solution was dried with anhydrous sodium sulfate, and concentrated under reduced pressure. The residue was purified with silica gel column chromatography, and from the fractions eluted with chloroform-methanol (19:1 v/v) was obtained 2.76 g of 1-benzyl-4-hydroxy-3-methylpiperidine, which was an oily product (yield: 69%).

(8-3)

2.33 g of 1-benzyl-4-hydroxy-3-methylpiperidine was dissolved in 50 ml of methanol, and a catalytic amount of palladium hydroxide-carbon was added to the solution. The solution was stirred overnight in hydrogen atmosphere, and after separating the catalyst by filtration, the residue was concentrated under reduced pressure to obtain 4-hydroxy-3-methylpiperidine, which was a yellow oily product. The resulting residue was dissolved in 15 ml of water and 45 ml of THF, and 1.62 ml of 2N aqueous solution of sodium hydroxide and benzyloxycarbonyl chloride was added to the solution in an ice bath. The resulting solution was stirred at room temperature for two hours, extracted with ethyl acetate, washed with water, saturated aqueous solution of sodium bicarbonate, and saturated aqueous solution of sodium chloride, and dried with anhydrous sodium sulfate. After separating the desiccant by filtration, the filtrate was concentrated under reduced pressure. The resulting residue was purified by silica gel column chromatography, and from the fractions eluted with chloroform-methanol (100:3 v/v) was obtained 2.60 g of N-benzyloxycarbonyl-4-hydroxy-3-methylpiperidine, which was an oily product (yield: 92%).

(8-4)

2.53 g of N-benzyloxycarbonyl-4-hydroxy-3-methylpiperidine was dissolved in 20 ml of toluene, and to this solution was added 2.96 g of tert-butyl bromoacetate, 0.1 g of tetrabutylammonium sulfate and 1 ml of water. Aqueous solution (10.1 g) of sodium hydroxide was added dropwise to this solution in an ice bath, and the solution was stirred overnight at room temperature. The resulting solution was washed with water and saturated solution of sodium chloride, and dried with anhydrous sodium sulfate. After separating the desiccant by filtration, the filtrate was concentrated under reduced pressure, and the resulting residue was purified by silica gel column chromatography. From the fractions eluted with chloroform-methanol (100:3 v/v) was obtained 1.59 g of N-benzyloxycarbonyl-4-tert-butoxycarbonylmethyloxy-3-methylpiperidine, which was an oily product (yield: 44%).

(8-5)

1.59 g of N-benzyloxycarbonyl-4-tert-butoxycarbonylmethyloxy-3-methylpiperidine was dissolved in 20 ml of methylene chloride, and 5 ml of trifluoroacetic acid was added to the solution. The solution was stirred overnight at room temperature, and the resulting solution was concentrated under reduced pressure to obtain N-benzyloxycarbonyl-4-carbonylmethyloxy-3-methylpiperidine, which was an oily product with no color. The concentrate was dissolved in 40 ml of DMF, and 1.93 g of BOP reagent, 1.09 g of 7-amino-2-(2-(ethoxycarbonyl) ethyl)-1,2,3,4-tetrahydroisoquinoline obtained in Example 2, and 1.33 g of triethylamine were added to this solution in an ice bath. The solution was stirred overnight at room temperature, and the resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the filtrate was concentrated under reduced pressure. The resulting residue was purified by silica gel column chromatography, and from the fractions eluted with chloroform-methanol (100:3 v/v) was obtained 1.14 g of 7-[1-(benzyloxycarbonyl)-2-methylpiperidine-4-yloxyacetylamino]-2-[2-(ethoxycarbonyl)ethyl]-1,2,3,4-tetrahydroisoquinoline, which was an oily product (yield: 49%).

(8-6)

0.50 g of 7-[1-(benzyloxycarbonyl)-2-methylpiperidine-4-yloxyacetylamino]-2-[2-(ethoxycarbonyl)ethyl]-1,2,3,4-tetrahydroisoquinoline was dissolved in 10 ml of methanol, and 0.26 g of potassium carbonate and 1 ml of water were added to the solution. The resulting solution was heated and stirred under reflux for two hours, acidified by adding dilute hydrochloric acid, concentrated under reduced pressure, and dissolved in anhydrous ethanol. The insoluble content was separated by filtration, and the filtrate was concentrated. The resulting residue was purified by silica gel column chromatography, and from the fractions eluted with chloroform-methanol (10:2 v/v) was obtained 0.43 g of 7-[1-(benzyloxycarbonyl)-3-methylpiperidine-4-yloxyacetylamino]-2-(2-carboxyethyl)-1,2,3,4-tetrahydroisoquinoline, which was an amorphous solid with no color (yield: 91%).

(8-7)

0.43 g of 7-[1-(benzyloxycarbonyl)-3-methylpiperidine-4-yloxyacetylamino]-2-(2-carboxyethyl)-1,2,3,4-tetrahydroisoquinoline was dissolved in 10 ml of methanol, and a catalytic amount of 10% palladium-carbon was added to the solution. The solution was stirred overnight in hydrogen atmosphere, and the catalyst was separated by filtration. The filtrate was concentrated under reduced pressure, to obtain 0.29 g of 7-(3-methylpiperidine-4-yloxyacetylamino)-2-(2-carboxyethyl)-1,2,3,4-tetrahydroisoquinoline, which was an amorphous solid with no color (yield: 92%). Instrumental analysis data of this product support the structural formula of formula 22, below.

$^1$H-NMR (CD$_3$OD) δ(ppm): 7.59 (s, 1H), 7.50–7.48 (m, 1H), 7.26–7.23 (m, 1H), 4.49 (s, 1H), 4.21 (dd, 2H, J=14.8, 36.0 Hz), 3.67–3.61 (m, 1H), 3.58 (t, 2H, J=6.8 Hz), 3.48–3.35 (m, 4H), 3.21–3.18 (m, 2H), 3.08–3.02 (m, 1H), 2.97 (t, 2H, J=6.8 Hz), 2.82–2.77 (m, 1H), 2.35–2.26 (m, 1H), 2.12–2.05 (m, 1H), 1.83–1.74 (m, 1H)

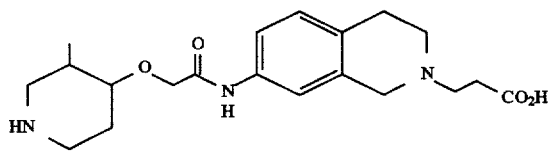

(22)

(EXAMPLE 9)

(9-1)

2.21 g of 7-nitro-1,2,3,4-tetrahydroisoquinoline hydrochloride was dissolved in 40 ml of ethanol, and to this solution were added 5.1 g of sodium bicarbonate, 1.55 g of separately synthesized 3-ethyl chlorobutanoate, and a catalytic amount of potassium iodide. The solution was heated and stirred overnight under reflux, and water was added to the reaction mixture. The mixture was extracted with ethyl acetate, washed with saturated aqueous solution of sodium chloride, and dried with anhydrous sodium sulfate. After separating the desiccant by filtration, the filtrate was concentrated under reduced pressure, and the resulting residue was purified by silica gel column chromatography. From the fractions eluted with chloroform-methanol (100:1 v/v) was obtained 0.43 g of 2-[2-(ethoxycarbonyl)-1-methylethyl]-7-nitro-1,2,3,4-tetrahydroisoquinoline, which was an oily product (yield: 14%).

(9-2)

0.43 g of 2-[2-(ethoxycarbonyl)-1-methylethyl]-7-nitro-1,2,3,4-tetrahydroisoquinoline was dissolved in 10 ml of ethanol, and 1.23 g of tin chloride dihydrate was added to the solution. The solution was heated under reflux for 30 minutes to allow for the reaction to take place. The resulting solution was made basic by adding saturated aqueous solution of sodium bicarbonate, and the insoluble content was separated by using celite. The solution was extracted with ethyl acetate, washed with saturated aqueous solution of sodium chloride, and dried with anhydrous sodium sulfate. After separating the desiccant by filtration, the residue was concentrated under reduced pressure to obtain 0.36 g of 7-amino-2-[2-(ethoxycarbonyl)-1-methylethyl]-1,2,3,4-tetrahydroisoquinoline, which was a brown oily product (yield: 93%).

(9-3)

0.36 g of 7-amino-2-[2-(ethoxycarbonyl)-1-methylethyl]-1,2,3,4-tetrahydroisoquinoline was dissolved in 30 ml of DMF, and 0.40 g of separately synthesized 1-(benzyloxycarbonyl)-4-(carboxymethoxy)piperidine, 0.67 g of BOP reagent, and 0.58 ml of triethylamine were added to the solution in an ice bath. The solution was stirred overnight at room temperature, and the resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the filtrate was concentrated under reduced pressure, and the resulting residue was purified by silica gel column chromatography. From the fractions eluted with chloroform-methanol (100:1 v/v) was obtained 0.73 g of 7-[1-(benzyloxycarbonyl)piperidine-4-yloxyacetylamino]-2-[2-(ethoxycarbonyl)-1-methylethyl]-1,2,3,4-tetrahydroisoquinoline, which was an oily product (yield: 99%).

(9-4)

0.41 g of 7-[1-(benzyloxycarbonyl)piperidine-4-yloxyacetylamino]-2-[2-(ethoxycarbonyl)-1-methylethyl]-1,2,3,4-tetrahydroisoquinoline was dissolved in 10 ml of methanol, and 0.25 g of potassium carbonate and 1 ml of water were added to the solution. The solution was heated under reflux with stirring for 3 hours. After acidifying the resulting solution by adding dilute hydrochloric acid, the solution was concentrated under reduced pressure, and dissolved in anhydrous ethanol. The insoluble content was separated by filtration, and the residue was purified by silica gel column chromatography. From the fractions eluted with chloroform-methanol (10:1 v/v) was obtained 0.25 g of 7-[1-(benzyloxycarbonyl)piperidine-4-yloxyacetylamino]-2-(2-carboxy-1-methylethyl)-1,2,3,4-tetrahydroisoquinoline, which was an amorphous solid with no color (yield: 65%).

(9-5)

0.25 g of 7-[1-(benzyloxycarbonyl)piperidine-4-yloxyacetylamino]-2-(2-carboxy-1-methylethyl)-1,2,3,4-tetrahydroisoquinoline was dissolved in 10 ml of methanol, and a catalytic amount of 10% palladium-carbon was added to the solution. The solution was stirred overnight in hydrogen atmosphere. The catalyst was separated by filtration, and the filtrate was concentrated to obtain 0.12 g of 7-(piperidine-4-yloxyacetylamino)-2-(2-carboxy-1-methylethyl)-1,2,3,4-tetrahydroisoquinoline, which was an amorphous solid with no color (yield: 69%). Instrumental analysis data of this product support the structural formula of formula 23, below.

$^1$H-NMR (CD$_3$OD) δ(ppm): 7.55 (s, 1H), 7.50 (d, 1H, J=6 Hz), 7.22 (d, 1H, J=6 Hz), 4.12 (s, 2H), 3.85–3.78 (m, 1H), 3.75 (s, 2H), 3.60–3.28 (m, 8H), 3.20–2.95 (m, 4H), 2.35–1.92 (m, 4H)

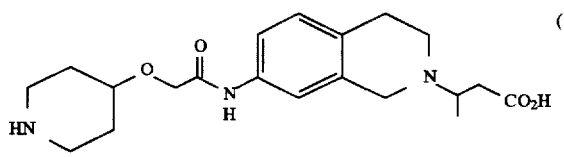

(23)

(EXAMPLE 10)

(10-1)

5.0 g of phenetylamine was dissolved in 50 ml of methylene chloride, and 7.0 ml of triethylamine and 3.6 ml of acetyl chloride were added to the solution at 0° C. The solution was stirred at room temperature for 2 hours, washed with water, aqueous solution of citric acid, and saturated aqueous solution of sodium chloride, and dried with anhydrous magnesium sulfate. After separating the desiccant by filtration, the solution was purified by silica gel column chromatography to obtain 5.52 g of N-acetylphenetylamine, which was white crystal (yield: 82%).

(10-2)

To 5.52 g of N-acetylphenetylamine was added 30.0 g of polyphosphoric acid at room temperature, and the solution was stirred at 200° C. for 2 hours. The reaction mixture was poured into ice, neutralized with aqueous solution of sodium hydroxide, and extracted with ethyl acetate. The organic layer was washed with saturated aqueous solution of sodium chloride, and dried with anhydrous sodium sulfate. The desiccant was separated by filtration, and purified by silica gel column chromatography to obtain 5.00 g of 1-methyl-3,4,-dihydroisoquinoline, which was a brown oily product (yield: 100%).

(10-3)

1.0 g of 1-methyl-3,4-dihydroisoquinoline was dissolved in 7.0 ml of conc. nitric acid at 0° C., and 14.0 ml of fuming nitric acid was added dropwise to the solution. The solution was stirred for one hour at the same temperature, and overnight at room temperature. The reaction mixture was poured into ice, neutralized with aqueous solution of sodium hydroxide, and extracted with ethyl acetate. The organic layer was washed with saturated aqueous solution of sodium chloride, and dried with anhydrous sodium sulfate. The desiccant was separated by filtration, and the filtrate was purified by silica gel column chromatography to obtain 1.08 g of 1-methyl-7-nitro-3,4-dihydroisoquinoline, which was white crystal (yield: 82%).

(10-4)

1.08 g of 1-methyl-7-nitro-3,4-dihydroisoquinoline was dissolved in 10 ml of methanol, and 0.43 g of sodium borohydride was added to the solution at 0° C. The solution was stirred overnight at room temperature, and water was added to the reaction mixture. The mixture was extracted with ethyl acetate, and after washing with saturated aqueous solution of sodium chloride, the solution was dried with anhydrous sodium sulfate. The desiccant was separated by filtration, and the filtrate was purified by silica gel column chromatography to obtain 0.90 g of 1-methyl-7-nitro-1,2,3,4-tetrahydroisoquinoline, which was an oily product (yield: 82%).

(10-5)

0.90 g of 1-methyl-7-nitro-1,2,3,4-tetrahydroisoquinoline was dissolved in 20 ml of ethanol, and 1.97 g of sodium bicarbonate, 2.55 g of ethyl bromopropionate, and a catalytic amount of potassium iodide were added to the solution. The solution was heated overnight under ref lux with stirring, and extracted with ethyl acetate. After washing with water and saturated aqueous solution of sodium chloride, the solution was dried with anhydrous sodium sulfate. The desiccant was separated by filtration, and the filtrate was purified by silica gel column chromatography to obtain 0.90 g of 2-[2-(ethoxycarbonyl)ethyl]-1-methyl-7-nitro-1,2,3,4-tetrahydroisoquinoline, which was an oily product (yield: 65%).

(10-6)

0.90 g of 2-[2-(ethoxycarbonyl)ethyl]-1-methyl-7-nitro-1,2,3,4-tetrahydroisoquinoline was dissolved in 10 ml of ethanol, and 2.78 g of tin chloride dihydrate was added to the solution. The solution was heated under reflux with stirring for 2 hours. The resulting solution was neutralized with aqueous solution of sodium bicarbonate, and extracted with ethyl acetate. After washing with water and saturated aqueous solution of sodium chloride, the solution was dried with anhydrous sodium sulfate. The desiccant was separated by filtration, and the solvent was distilled off to obtain 0.69 g of 7-amino-2-[2-(ethoxycarbonyl)ethyl]-1-methyl-1,2,3,4-tetrahydroisoquinoline, which was an oily product. This product with no further purification was dissolved in 10 ml of DMF, and to this solution were added 0.92 g of separately synthesized 1-(benzyloxycarbonyl)-4-(carboxymethoxy) piperidine and 0.75 g of 1-ethyl-3-(3-dimethylaminopropyl) carbodiimide. The solution was stirred overnight at room temperature, and the resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the filtrate was purified by silica gel column chromatography to obtain 1.00 g of 7-[1-(benzyloxycarbonyl)piperidine-4-yloxyacetylamino]-2-[2-(ethoxycarbonyl)ethyl]-1-methyl-1,2,3,4-tetrahydroisoquinoline, which was an oily product (yield: 71%).

(10-7)

1.00 g of 7-[1-(benzyloxycarbonyl)piperidine-4-yloxyacetylamino]-2-[2-(ethoxycarbonyl)ethyl]-1-methyl-1,2,3,4-tetrahydroisoquinoline was dissolved in 5 ml of ethanol, and 2.0 ml of 2N aqueous solution of sodium hydroxide was added to the solution. The solution was stirred overnight at room temperature. The resulting solution was acidified, concentrated under reduced pressure, and dissolved in anhydrous ethanol. The insoluble content was separated by filtration, and the solvent was distilled off. The residue was purified by silica gel column chromatography to obtain 0.59 g of 7-[1-(benzyloxycarbonyl)piperidine-4-yloxyacetylamino]-2-(2-carboxyethyl)-1-methyl-1,2,3,4-tetrahydroisoquinoline hydrochloride, which was amorphous solid (yield: 62%).

(10-8)

0.59 g of 7-[1-(benzyloxycarbonyl)piperidine-4-yloxyacetylamino]-2-(2-carboxyethyl)-1-methyl-1,2,3,4-tetrahydroisoquinoline hydrochloride was dissolved in 10 ml of methanol, and a catalytic amount of 10% palladium-carbon was added to the solution. The solution was stirred overnight in hydrogen atmosphere, and the catalyst was separated by filtration. The solvent was distilled off under reduced pressure, and the residue was purified by silica gel column chromatography to obtain 0.20 g of 2-(2-carboxyethyl)-1-methyl-7-(piperidine-4-yloxyacetylamino)-1,2,3,4-tetrahydroisoquinoline hydrochloride, which was amorphous solid with no color (yield: 42%). Instrumental analysis data of this product support the structural formula of formula 24, below.

$^1$H-NMR (CD$_3$OD) δ(ppm): 7.60 (s, 1H), 7.54–7.51 (d, 1H, J=8.4 Hz), 7.39–7.34 (d, 1H, J=8.4 Hz), 4.48 (s, 2H), 3.98–3.80 (m, 2H), 3.60–3.12 (m, 10H), 2.95–2.87 (t, 2H, J=6.4 Hz), 2.18–1.98 (m, 4H), 1.36–1.30 (d, 3H, J=10.0 Hz)

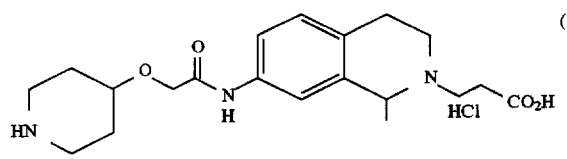

(24)

(EXAMPLE 11)

(11-1)

3.22 g of ethyl formate was added dropwise to 4.90 g of β-methylphenetylamine at 0° C., and the reaction was allowed to proceed at the same temperature for 30 minutes, and under reflux at an elevated temperature for 2 hours. The excess amount of ethyl formate was distilled off under reduced pressure, and the residue was purified by silica gel column chromatography to obtain 6.18 g of N-formyl-β-methylphenetylamine, which was an oily product (yield: 100%).

(11-2)

The procedure of Example 10 was repeated by using 6.18 g of β-methylphenetylamine and 60.0 g of polyphosphoric acid to obtain 4.91 g of 4-methyl-3,4-dihydroisoquionline, which was a brown oily product (yield: 89%).

(11-3)

2.00 g of 4-methyl-3,4-dihydroisoquionline was dissolved in 20 ml of ethanol, and a catalytic amount of 10% palladium-carbon was added to the solution. The solution was stirred overnight in hydrogen atmosphere, and the catalyst was separated by filtration. The solvent was distilled off under reduced pressure to obtain 2.13 g of 4-methyl-1,2,3,4-tetrahydroisoquinoline, which, with no further purification, was dissolved in 7.0 ml of conc. sulfuric acid. 1.53 g of potassium nitrate was slowly added to this solution in an ice bath, and the solution was stirred for 1 hour at the same temperature, and overnight at room temperature. The reaction mixture was poured into ice, neutralized with aqueous solution of sodium hydroxide, and extracted with ethyl acetate. The organic layer was washed with saturated aqueous solution of sodium chloride, and dried with anhydrous sodium sulfate. After separating the desiccant by filtration, the filtrate was purified by silica gel column chromatography to obtain 1.97 g of 4-methyl-7-nitro-1,2,3,4-tetrahydroisoquinoline, which was an oily product with no color (yield: 74%)

(11-4)

The procedure of Example 2 was repeated by using 2.28 g of 4-methyl-7-nitro-1,2,3,4-tetrahydroisoquinoline, 2.99 g of sodium bicarbonate, 3.22 g of ethyl bromopropionate, and a catalytic amount of potassium iodide to obtain 2.52 g of 2-[2-(ethoxycarbonyl)ethyl]-4-methyl-7-nitro-1,2,3,4-tetrahydroisoquinoline, which was an oily product (yield: 73%).

(11-5)

Reduction was effected by using 2.39 g of 2-[2-(ethoxycarbonyl)ethyl]-4-methyl-7-nitro-1,2,3,4-tetrahydroisoquinoline and 7.38 g of tin chloride dihydrate, and the procedure of Example 2 was repeated by using 2.86 g of 1-(benzyloxycarbonyl)-4-(carboxymethoxy)piperidine and 2.33 g of 1-ethyl-3-(3-dimethylaminopropyl) carbodiimide to obtain 3.80 g of 7-[1-(benzyloxycarbonyl)piperidine-4-yloxyacetylamino]-2-[2-(ethoxycarbonyl)ethyl]-4-methyl-1,2,3,4-tetrahydroisoquinoline, which was an oily product (yield: 87%).

(11-6)

The procedure of Example 2 was repeated by using 3.80 g of 7-[1-(benzyloxycarbonyl)piperidine-4-yloxyacetylamino]-2-[2-(ethoxycarbonyl)ethyl]-4-methyl-1,2,3,4-tetrahydroisoquinoline and 7.1 ml of 2N aqueous solution of sodium hydroxide to obtain 3.17 g of 7-[1-(benzyloxycarbonyl)piperidine-4-yloxyacetylamino]-2-(2-carboxyethyl)-4-methyl-1,2,3,4-tetrahydroisoquinoline hydrochloride, which was amorphous solid (yield: 82%).

(11-7)

The procedure of Example 2 was repeated by using 3.17 g (5.8 mmol) of 7-[1-(benzyloxycarbonyl)piperidine-4-yloxyacetylamino]-2-(2-carboxyethyl)-4-methyl-1,2,3,4-tetrahydroisoquinoline hydrochloride to obtain 2.36 g of 2-(2-carboxyethyl)-4-methyl-7-(piperidine-4-yloxyacetylamino)-1,2,3,4-tetrahydroisoquinoline hydrochloride, which was amorphous solid with no color (yield: 98%). Instrumental analysis data of this product support the structural formula of formula 25, below.

$^1$H-NMR (CD$_3$OD) δ(ppm): 7.60–7.55 (m, 3H), 7.41–7.36 (d, 1H, J=7.2 Hz), 4.47 (s, 2H), 4.14 (s, 2H), 3.88–3.82 (m, 1H), 3.79–3.70 (m, 1H), 3.60–3.52 (t, 2H, J=6.8 Hz), 3.46–3.32 (m, 4H), 3.22–3.10 (m, 2H), 2.97–2.90 (t, 2H, J=6.8 Hz), 2.18–1.98 (m, 4H), 1.44–1.39 (d, 3H, J=6.8 Hz)

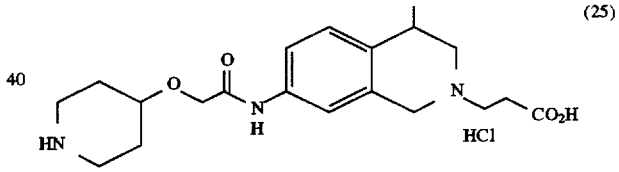

(25)

(EXAMPLE 12)

(12-1)

The procedure of Example 11 was repeated by using 5.00 g of (α,α-dimethylphenetylamine and 2.98 g of ethyl formate to obtain 4.31 g of N-formyl-α,α-dimethylphenetylamine, which was an oily product (yield: 73%).

(12-2)

The procedure of Example 11 was repeated by using 3.94 g of N-formyl-α,α-dimethylphenetylamine and 40.0 g of polyphosphoric acid to obtain 0.58 g of 3,3-dimethyl-3,4-dihydroisoquionline, which was a brown oily product (yield: 16%).

(12-3)

0.58 g of 3,3-dimethyl-3,4-dihydroisoquionline was reduced by catalytic hydrogenation and added to 2.0 ml of conc. sulfuric acid, and the procedure of Example 11 was repeated by using 0.35 g of potassium nitrate to obtain 0.48 g of 3,3-dimethyl-7-nitro-1, 2,3,4-tetrahydroisoquinoline, which was a brown oily product (yield: 64%).

(12-4)

The procedure of Example 11 was repeated by using 0.28 g of 3,3-dimethyl-7-nitro-1,2,3,4-tetrahydroisoquinoline, 0.29 g of sodium bicarbonate, 0.32 g of ethyl bromopropionate, and a catalytic amount of potassium iodide to obtain 0.12 g of 3,3-dimethyl-2-[2-(ethoxycarbonyl)ethyl]-7-nitro-1,2,3,4-tetrahydroisoquinoline, which was an oily product (yield: 34%).

(12-5)

Reduction was effected by using 0.12 g of 3,3-dimethyl-2-[2-(ethoxycarbonyl)ethyl]-7-nitro-1,2,3,4-tetrahydroisoquinoline and 0.35 g of tin chloride dihydrate, and the procedure of Example 1 was repeated by using 0.14 g of 1-(benzyloxycarbonyl)-4-(carboxymethoxy)piperidine and 0.12 g of 1-ethyl-3-(3-dimethylaminopropyl)carbodiimide to obtain 0.14 g of 7-[1-(benzyloxycarbonyl)piperidine-4-yloxyacetylamino]-3,3-dimethyl-2-[2-(ethoxycarbonyl)ethyl]-1,2,3,4-tetrahydroisoquinoline, which was an oily product (yield: 66%).

(12-6)

The procedure of Example 1 was repeated by using 0.14 g of 7-[1-(benzyloxycarbonyl)piperidine-4-yloxyacetylamino]-3,3-dimethyl-2-[2-(ethoxycarbonyl)ethyl]-1,2,3,4-tetrahydroisoquinoline and 0.3 ml of 2N aqueous solution of sodium hydroxide to obtain 0.13 g of 7-[1-(benzyloxycarbonyl)piperidine-4-yloxyacetylamino]-2-(2-carboxyethyl)-3,3-dimethyl-1,2,3,4-tetrahydroisoquinoline hydrochloride, which was amorphous solid (yield: 96%).

(12-7)

The procedure of Example 1 was repeated by using 0.13 g of 7-[1-(benzyloxycarbonyl)piperidine-4-yloxyacetylamino]-2-(2-carboxyethyl)-3,3-dimethyl-1,2,3,4-tetrahydroisoquinoline hydrochloride to obtain 0.07 g of 2-(2-carboxyethyl)-3,3-dimethyl-7-(piperidine-4-yloxyacetylamino)-1,2,3,4-tetrahydroisoquinoline hydrochloride which was amorphous solid with not color (yield: 74%). Instrumental analysis data of this product support the structural formula of formula 26, below.

¹H-NMR (CD₃OD) δ(ppm): 7.61 (s, 1H), 7.55–7.50 (d, 1H, J=8.4 Hz), 7.21–7.17 (d, 1H, J=8.4 Hz), 4.50 (s, 2H), 4.20 (s, 2H), 3.86–3.80 (m, 1H), 3.56–3.47 (t, 2H, J=6.4 Hz), 3.47–3.36 (m, 2H), 3.19–3.07 (m, 4H), 2.94–2.86 (t, 3H, J=6.4 Hz), 2.18–1.97 (m, 4H), 1.51 (s, 6H)

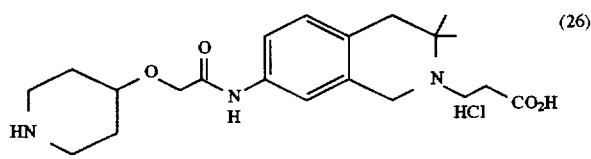

(26)

(EXAMPLE 13)

1.08 g of 7-(piperidine-4-yloxyacetylamino)-2-(2-(ethoxycarbonyl)ethyl)-1,2,3,4-tetrahydroisoquinoline was dissolved in 10 ml of DMF, and to this solution was added a solution (5 ml) of (acetoxy)methyl 4-nitrophenylcarbonate in DMF. The solution was stirred at room temperature for 22 hours, and water was added to the solution. The solution was extracted with ethyl acetate, washed with 8% aqueous solution of sodium hydroxide and water, and dried with sodium sulfate. The solvent was distilled off under reduced pressure, and the residue was dissolved in 10 ml of ethanol. Hydrochloric acid gas was introduced in the solution, and the solution was allowed to stand. The resulting crystals were separated by filtration to obtain 0.57 g of 7-((N-(acetoxymethoxycarbonyl)piperidine)-4-yloxyacetylamino)-2-(2-(ethoxycarbonyl)ethyl)-1,2,3,4-tetrahydroisoquinoline hydrochloride (yield: 38%). Instrumental analysis data of this product support the structural formula of formula 27, below, melting point 116°–117° C.

¹H-NMR (CD₃OD) d/ppm: 7.62 (s, 1H), 7.44 (d, J=8.4 Hz, 1H), 7.24 (d, J=8.4 Hz, 1H), 5.72 (s, 2H), 4.46 (brs, 1H), 4.22 (q, J=7.2 Hz, 2H), 4.15 (s, 2H), 3.87–3.12 (m, 11H), 2.97 (t, J=7.2 Hz, 2H), 2.07 (s, 3H), 2.00–1.88 (m, 2H), 1.70–1.59 (m, 2H), 1.29 (t, J=7.2 Hz, 3H)

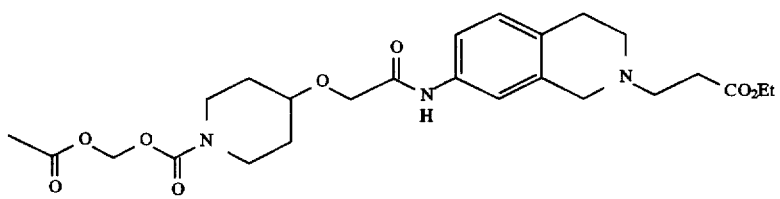

(27)

(EXAMPLE 14)

0.60 g of 7-(piperidine-4-yloxyacetylamino)-2-(2-(ethoxycarbonyl)ethyl)-1,2,3,4-tetrahydroisoquinoline was dissolved in 5 ml of DMF, and to this solution was added a solution (3 ml) of 1-(acetoxy)ethyl 4-nitrophenylcarbonate in DMF. The solution was stirred at room temperature for 22 hours, and water was added to the solution. The solution was extracted with ethyl acetate, washed with 8% aqueous solution of sodium hydroxide and water, and dried with magnesium sulfate. The solvent was distilled off under reduced pressure, and the residue was treated by silica gel column chromatography to obtain 0.61 g of 7-((N-(1-acetoxy)ethoxycarbonyl)piperidine)-4-yloxyacetylamino)-2-(2-(ethoxycarbonyl)ethyl)-1,2,3,4-tetrahydroisoquinoline, which was an orange oily product (yield: 76%). Instrumental analysis data of this product support the structural formula of formula 28, below.

¹H-NMR (CD₃OD) d/ppm: 8.26 (s, 1H), 7.31 (d, J=2.0 Hz, 1H), 7.25 (J=8.4 Hz, 1H), 7.02 (d, J=8.4 Hz, 1H), 6.79 (q, J=5.2 Hz, 1H), 4.13 (q, J=7.1 Hz, 2H), 4.05 (s, 2H), 3.83–3.79 (m, 2H), 3.69 (t, J=7.3 Hz, 2H), 3.61 (s, 2H), 3.67–3.61 (m, 1H), 3.24–3.18 (m, 2H), 2.85–2.82 (m, 4H), 2.73 (t, J=6.0 Hz, 2H), 2.56 (t, J=7.3 Hz, 2H), 2.05 (s, 3H), 1.95–1.89 (m, 2H), 1.68–1.59 (m, 2H), 1.48 (d, J=5.2 Hz, 3H), 1.23 (t, J=7.1 Hz, 3H)

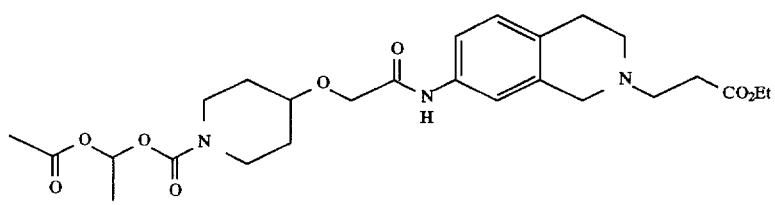

(EXAMPLE 15)

0.64 g of 7-(piperidine-4-yloxyacetylamino)-2-(2-(ethoxycarbonyl)ethyl)-1,2,3,4-tetrahydroisoquinoline was dissolved in 5 ml of DMF, and to this solution was added a

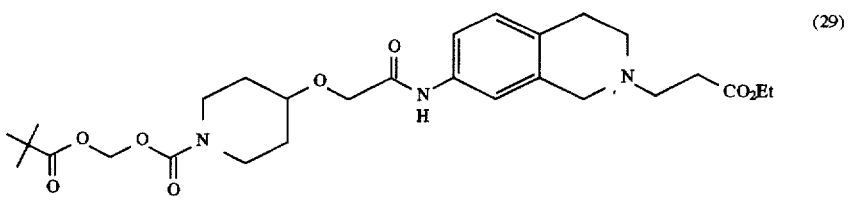

solution (9 ml) of (pivaloyloxy)methyl 4-nitrophenylcarbonate in DMF. The solution was stirred at room temperature for 18 hours, and water was added to the solution. The solution was extracted with ethyl acetate, washed with 8% aqueous solution of sodium hydroxide and water, and dried with magnesium sulfate. The solvent was distilled off under reduced pressure, and the residue was treated by silica gel column chromatography to obtain 0.75 g of 7-((N-(pivaloyloxymethoxycarbonyl)piperidine)-4-yloxyacetylamino)-2-(2-(ethoxycarbonyl)ethyl)-1,2,3,4-tetrahydroisoquinoline, which was an orange oily product (yield: 84%).

This product was dissolved in 2 ml of ethyl acetate, and to the solution was added ethanol solution (2 ml) of 0.37 g of toluenesulfonic acid monohydrate. Diethylether was added to this solution to precipitate crystals, and the crystals were collected by filtration. There was obtained 0.71 g of 7-((N-(pivaloyloxymethoxycarbonyl)piperidine)-4-yloxyacetylamino)-2-(2-(ethoxycarbonyl)ethyl)-1,2,3,4-tetrahydroisoquinoline toluenesulfonate, which was pale yellow crystals. Instrumental analysis data of this product support the structural formula of formula 29, below. melting point 100°–101° C.

$^1$H-NMR (CD$_3$OD) d/ppm: 11.43 (bs, 1H), 8.41 (s, 1H), 7.58 (d, J=8.0 Hz, 2H), 7.49 (s, 1H), 7.41 (d, J=8.0 Hz, 1H), 7.14 (d, J=8.0 Hz, 1H), 7.09 (d, J=8.0 Hz, 2H), 5.78 (s, 2H), 4.63–4.58 (m, 1H), 4.16 (q, J=7.2 Hz, 2H), 4.09 (s, 2H), 4.11–4.05 (m, 2H), 3.91–3.80 (m, 2H), 3.78–3.72 (m, 1H), 3.68–3.62 (m, 1H), 3.53–3.44 (m, 2H), 3.39–3.18 (m, 5H), 3.03 (t, J=7.6 Hz, 2H), 3.00–2.94 (m, 1H), 2.32 (s, 3H), 1.98–1.86 (m, 2H), 1.69–1.59 (m, 2H), 1.26 (t, J=7.2 Hz, 3H), 1.22 (s, 9H)

(EXAMPLE 16)

0.30 g of 7-(piperidine-4-yloxyacetylamino)-2-(2-(ethoxycarbonyl)ethyl)-1,2,3,4-tetrahydroisoquinoline di-hydrobromate was dissolved in 5 ml of DMF, and to this solution was added 0.30 g of potassium carbonate, and 0.09 g of hexyl chlorocarbonate, in this order. The solution was stirred at room temperature for 2 hours, and water was added to the solution. The solution was extracted with ethyl acetate, washed with 8% aqueous solution of sodium hydroxide and water, and dried with sodium sulfate. The solvent was distilled off under reduced pressure, and the residue was purified by silica gel column chromatography to obtain 0.24 g of 7-((N-(hexyloxycarbonyl)piperidine)-4-yloxyacetylamino)-2-(2-(ethoxycarbonyl)ethyl)-1,2,3,4-tetrahydroisoquinoline hydrochloride (yield: 87%). Instrumental analysis data of this product support the structural formula of formula 30, below.

$^1$H-NMR (CDCl$_3$) d/ppm: 8.28 (s, 1H), 7.32 (s, 1H), 7.25 (d, J=8.2 Hz, 1H), 7.03 (d, J=8.2 Hz, 1H), 4.13 (q, 6.9 Hz, 2H), 4.08–4.05 (m, 4H), 3.86–3.83 (m, 2H), 3.64–3.59 (m, 3H), 3.20–3.13 (m, 2H), 2.86–2.81 (m, 4H), 2.73 (t, J=6.2 Hz, 2H), 2.57 (t, 7.3 Hz, 2H), 1.93–1.89 (m, 2H), 1.67–1.55 (m, 4H), 1.39–1.28 (m, 6H), 1.25 (t, J=6.9 Hz, 3H), 0.89 (t, J=6.8 Hz, 3H)

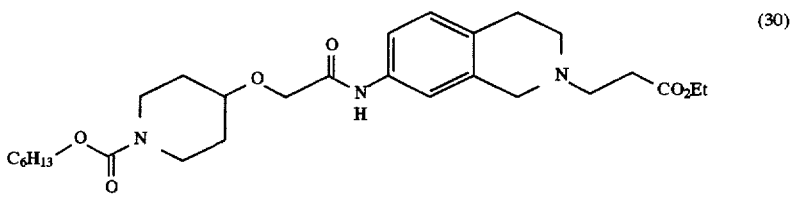

(EXAMPLE 17)

(17-1)

3.51 g of 2-(2-(ethoxycarbonyl)ethyl)-7-nitro-1,2,3,4-tetrahydroisoquinoline was dissolved in 100 ml of ethanol, and 13.0 ml of 2N aqueous solution of sodium hydroxide was added to the solution. The solution was stirred overnight at room temperature. Dilute hydrochloric acid was added dropwise to the resulting solution to acidify the solution, and the solution was concentrated under reduced pressure, and dissolved in anhydrous ethanol. The insoluble content was separated by filtration, and the solvent was distilled off to obtain crude crystals of 2-(2-carboxyethyl)-7-nitro-1,2,3,4- tetrahydroisoquinoline. The crystals, with no further purification, were dissolved in 20 ml of DMF, and the solution was neutralized by adding 1.8 ml of triethylamine. To this solution were added 1.93 g of benzylalcohol, 3.42 g of 1-ethyl-3-(3-dimethylaminopropyl)carbodiimide, and 1.93 g of 1-hydroxybenzotriazol, and the solution was stirred overnight at room temperature. The resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the filtrate was purified by silica gel column chromatography to obtain 1.60 g of 2-(2-benzyloxycarbonylethyl)-7-nitro-1,2,3,4-tetrahydroisoquinoline, which was an oily product (yield: 49%).

(17-2)

1.80 g of 2-(2-benzyloxycarbonylethyl)-7-nitro- 1,2,3,4-tetrahydroisoquinoline was dissolved in 10 ml of ethanol, and 4.77 g of tin chloride dihydrate was added to the solution. The solution was heated under reflux with stirring for 30 minutes. The resulting solution was neutralized by adding saturated aqueous solution of sodium bicarbonate, and the solution was extracted with ethyl acetate, washed with water and saturated aqueous solution of sodium chloride, and dried with anhydrous sodium sulfate. After separating the desiccant by filtration, the residue was purified by silica gel column chromatography to obtain 1.52 g of 7-amino-2-(2-benzyloxycarbonylethyl)-1,2,3,4-tetrahydroisoquinoline as an oily product. This product, with no further purification, was dissolved in 10 ml of DMF, and 1.52 g of 1-(tertbutoxycarbonyl)-4-(carboxymethoxy)piperidine and 0.41 g of 1-ethyl-3-(3-dimethylaminopopyl) carbodiimide, which had been separately synthesized, were added to this solution. The solution was stirred overnight at room temperature. The resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the residue was purified by silica gel column chromatography to obtain 1.84 g of 2-(2-benzyloxycarbonylethyl)-7-[1-(tert-butoxycarbonyl)piperidine-4-yloxyacetylamino]-1,2,3,4-tetrahydroisoquinoline, which was an oily product (yield: 68%).

(17-3)

1.84 g of 2-(2-benzyloxycarbonylethyl)-7-[1-(tertbutoxycarbonyl)piperidine-4-yloxyacetylamino]-1,2,3, 4-tetrahydroisoquinoline was dissolved in 20 ml of methylene chloride, and 5.2 ml of trifluoroacetic acid was added to the solution at 0° C. The solution was stirred at the same temperature for 2 hours, and the reaction solution was concentrated at reduced pressure to obtain 3.92 g of 2-(benzyloxycarbonylethyl)-7-(piperidine-4-yloxyacetylamino)-1,2,3,4-tetrahydroisoquinoline trifluoroacetate. This product, with no further purification, was dissolved in 10 ml of DMF, and the solution was neutralized by adding 1.4 ml of triethylamine. 1.03 g of separately synthesized (acetoxy)methyl 4-nitrophenylcarbonate was added to the solution, and the solution was stirred overnight at room temperature. The resulting solution was extracted with ethyl acetate, washed with water, saturated aqueous solution of sodium bicarbonate, and saturated aqueous solution of sodium chloride, and dried with anhydrous sodium sulfate. After separating the desiccant by filtration, the residue was purified by silica gel column chromatography to obtain 1.78 g of 7-[1-(acetoxymethoxycarbonyl)piperidine-4-yloxyacetylamino]-2-(2-benzyloxycarbonylethyl)-1,2,3, 4-tetrahydroisoquinoline, which was an oily product (yield: 94%).

(17-4)

1.78 g of 7-[1-(acetoxymethoxycarbonyl)piperidine-4-yloxylacetylamino]-2-(2-benzyloxycarbonylethyl)-1,2,3,4-tetrahydroisoquinoline was dissolved in 50 ml of ethanol, and a catalytic amount of 10% palladium-carbon was added to the solution. The solution was stirred overnight in hydrogen atmosphere, and the catalyst was separated by filtration. After distilling off the solvent under reduced pressure, the residue was purified by silica gel column chromatography to obtain 1.40 g of 7-[1-(acetoxymethoxycarbonyl)piperidine-4-yloxylacetylamino]-2-(2-carboxyethyl)-1,2,3,4-tetrahydroisoquinoline, which was an amorphous solid with no color (yield: 93%). Instrumental analysis data of this product support the structural formula of formula 31, below.

¹H-NMR (CD₃OD) δ(ppm): 7.54 (s, 1H), 7.54–7.38 (d, 1H, J=8.0 Hz), 7.22–7.16 (d, 1H, J=8.0 Hz), 4.24 (s, 2H), 4.12 (s, 2H), 3.90–3.62 (m, 3H), 3.44–2.98 (m, 10H), 2.72–2.54 (t, 3H, J=7.2 Hz), 2.08 (s, 3H), 2.04–1.82 (m, 2H), 1.74–1.54 (m, 2H)

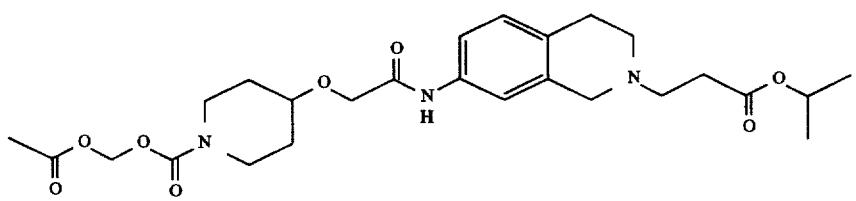

(31)

(EXAMPLE 18)

(18-1)

To the solution (60 ml) in ethanol of 2.04 g of 2-(2-(ethoxycarbonyl)ethyl)-7-nitro-1,2,3,4-tetrahydroisoquinoline obtained in Example 2 was added 3.75 ml of 2N aqueous solution of sodium hydroxide, and the solution was stirred at room temperature for 14 hours. The solution was concentrated under reduced pressure, and to the residue were added 300 ml of isopropylalcohol and 0.60 ml of sulfuric acid. The solution was heated under reflux for 20 hours, and concentrated under reduced pressure. After adding saturated aqueous solution of sodium bicarbonate to the residue, the solution was extracted with ethyl acetate, washed with water, dried with anhydrous sodium sulfate, and concentrated under reduced pressure. The residue was purified by silica gel column chromatography to obtain 1.58 g of 2-(2-(isopropyloxycarbonyl)ethyl) -7-nitro-1,2,3,4-tetrahydroisoquinoline (yield: 74%).

(18-2)

The suspension (60 ml) in methanol of 1.58 g of 2-(2-(isopropyloxycarbonyl)ethyl)-7-nitro-1,2,3,4-tetrahydroisoquinoline and 1.0 g of palladium-carbon (10%) was stirred for one day, and the catalyst was separated by filtration. The filtrate was concentrated under reduced pressure to obtain 1.11 g of 7-amino-2-(isopropyloxycarbonyl) ethyl)-1,2,3,4-tetrahydroisoquinoline (yield: 78%).

(18-3)

1.11 g of 7-amino-2-(isopropyloxycarbonyl)ethyl)-1,2,3,4-tetrahydroisoquinoline was dissolved in 15 ml of DMF, and 1.27 g of 1-(benzyloxycarbonyl)-4-(carboxymethoxy)piperidine and 2.07 g of BOP reagent were added to the solution. 1.77 ml of triethylamine was added to the solution in an ice bath, and the solution was stirred for 4 hours at room temperature. After adding water to the solution, the solution was extracted with ethyl acetate, dried with anhydrous sodium sulfate, and concentrated under reduced pressure. The residue was purified by silica gel column chromatography to obtain 1.95 g of 7-(1-(benzyloxycarbonyl)piperidine-4-yloxyacetylamino)-2-(isopropyloxycarbonyl)ethyl)-1,2,3,4-tetrahydroisoquinoline (yield: 84%).

(18-4)

The suspension (50 ml) in methanol of 1.95 g of 7-(1-(benzyloxycarbonyl)piperidine-4-yloxyacetylamino)-2-(2-(isopropyloxycarbonyl)ethyl)-1,2,3,4-tetrahydroisoquinoline and 1.0 g of palladium-carbon (10%) was stirred for one day, and the catalyst was separated by filtration. The filtrate was concentrated under reduced pressure, and the residue was dissolved in ethanol. To the solution were added 1.18 g of tosyl acid, and then ether. The thus precipitated crystals were collected to obtain 1.97 g of 7-(piperidine-4-yloxyacetylamino)-2-(2-(isopropyloxycarbonyl)ethyl)-1,2,3,4-tetrahydroisoquinoline tosylate (yield: 73%). Instrumental analysis data of this product support the structural formula of formula 32, below. melting point: 196°–198° C.

$^1$H-NMR (D$_2$O) d/ppm: 7.66 (d, 4H, J=8.4 Hz), 7.34 (d, J=8.4 Hz, 4H), 7.30 (s, 1H), 5.75–5.00 (m, 1H), 4.50–4.32 (brs, 2H), 4.25 (s, 2H), 3.90–3.82 (m, 1H), 3.68–3.52 (m, 4H), 3.46–3.38 (m, 2H), 3.22–3.10 (m, 4H), 2.96 (t, J=6.8 Hz, 2H), 2.37 (s, 6H), 2.20–2.10 (m, 2H), 1.98–1.86 (m, 2H), 1.26 (d, J=6.4 Hz, 6H)

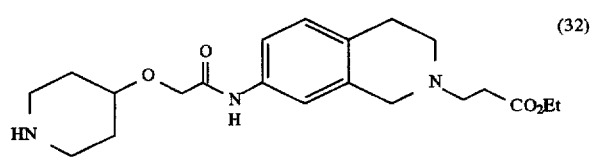

(32)

(EXAMPLE 19)

(19-1)

To the solution (20 ml) in methanol of 1.51 g of 7-(1-(benzyloxycarbonyl)piperidine-4-yloxyacetylamino)-2-(2-(ethoxycarbonyl)ethyl)-1,2,3,4-tetrahydroisoquinoline obtained in Example 2 was added 2 ml of aqueous solution of 0.79 g of potassium carbonate, and the solution was heated under reflux for 2 hours. The solution was concentrated under reduced pressure, acidified by adding dilute hydrochloric acid, and further concentrated under reduced pressure. Ethanol was added to the residue, and the precipitate formed was separated by filtration. The residue was concentrated under reduced pressure to obtain 1.53 g of 7-(1-(benzyloxycarbonyl)piperidine-4-yloxyacetylamino)-2-(2-(carboxy)ethyl)-1,2,3,4-tetrahydroisoquinoline hydrochloride (yield: 100%).

(19-2)

To a solution in DMF of 0.56 g of 7-(1-(benzyloxycarbonyl)piperidine-4-yloxyacetylamino)-2-(2-(carboxy)ethyl)-1,2,3,4-tetrahydroisoquinoline hydrochloride were added 0.30 g of potassium carbonate and 0.26 g of iodomethyl pivaloate, and the solution was stirred for 10 hours at room temperature. Ethyl acetate was added to the solution, and the solution was washed with water, dried with anhydrous sodium sulfate, and concentrated under reduced pressure. The residue was purified by silica gel column chromatography to obtain 0.28 g of 7-(1-(benzyloxycarbonyl)piperidine-4-yloxyacetylamino)-2-(2-(pivaloyloxymethoxycarbonyl)ethyl)-1,2,3,4-tetrahydroisoquinoline (yield: 44%).

(19-3)

1 ml of hydrobromic acid-acetic acid solution was added to 96.9 mg of 7-(1-(benzyloxycarbonyl)piperidine-4-yloxyacetylamino)-2-(2-(pivaloyloxymethoxycarbonyl)ethyl)-1,2,3,4-tetrahydroisoquinoline, and the solution was stirred for 1 hour. Ether was added to the solution, and the precipitated crystals were separated by filtration to obtain 101 mg of 7-(piperidine-4-yloxyacetylamino)-2-(2-(pivaloyloxymethoxycarbonyl)ethyl)-1,2,3,4-tetrahydroisoquinoline di-hydrobromate (yield: 100%). Instrumental analysis data of this product support the structural formula of formula 33, below.

$^1$H-NMR (D$_2$O) d/ppm: 7.31 (s, 3H), 5.81 (s, 2H), 4.58–4.36 (s, 2H), 4.26 (s, 2H), 3.90–3.84 (m, 1H), 3.70–3.05 (m, 10H), 2.20–2.10 (m, 2H), 1.98–1.88 (m, 2H), 1.18 (s, 9H)

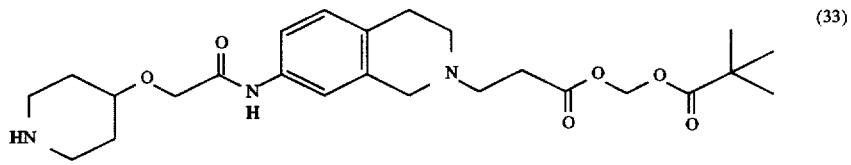

(33)

(EXAMPLE 20)

(20-1)

To a solution in DMF of 0.51 g of 7-(1-(benzyloxycarbonyl)piperidine- 4-yloxyacetylamino)-2-(2-(carboxy)ethyl)-1,2,3,4-tetrahydroisoquinoline hydrochloride obtained in Example 19 were added 0.34 g of potassium carbonate and 0.38 g of cyclohexyl 1-iodoethyl carbonate, and the solution was stirred at room temperature for 10 hours. Ethyl acetate was added to the solution, and the solution was washed with water, dried with anhydrous sodium sulfate, and concentrated under reduced pressure. The residue was purified by silica gel column chromatography to obtain 0.23 g of 7-(1-(benzyloxycarbonyl)piperidine-4-yloxyacetylamino)-2-(2-(1-(cyclohexyloxycarbonyloxy)ethoxycarbonyl)ethyl)-1,2,3,4-tetrahydroisoquinoline (yield: 35%).

(20-2)

1 ml of hydrobromic acid-acetic acid solution was added to 0.23 g of 7-(1-(benzyloxycarbonyl)piperidine-4-yloxyacetylamino)-2-(2-(1-(cyclohexyloxycarbonyloxy)ethoxycarbonyl)ethyl)-1,2,3,4-tetrahydroisoquinoline, and the solution was stirred for 1 hour. Ether was added to the solution, and the precipitated crystals were separated by filtration to obtain 115 mg of 7-(piperidine-4-yloxyacetylamino)-2-(2-(1-(cyclohexyloxycarbonyloxy)ethoxycarbonyl)ethyl)-1,2,3,4-tetrahydroisoquinoline di-hydrobromate (yield: 48%). Instrumental analysis data of this product support the structural formula of formula 34, below.

$^1$H-NMR (D$_2$O) d/ppm: 7.37–7.29 (m, 3H), 6.77 (q, J=5.6 Hz, 1H), 4.65–4.59 (m, 1H), 4.58–4.32 (m, 3H), 4.26 (s, 2H), 3.91–3.85 (m, 1H), 3.68–3.61 (m, 2H), 3.47–3.39 (m, 2H), 3.24–3.12 (m, 6H), 3.08 (t, J=6.8 Hz, 2H), 2.21–2.13 (m, 2H), 1.99–1.89 (m, 2H), 1.88–1.78 (m, 2H), 1.70–1.59 (m, 2H), 1.54 (d, 3H, 5.6 Hz), 1.51–1.39 (m, 2H), 1.38–1.19 (m, 4H)

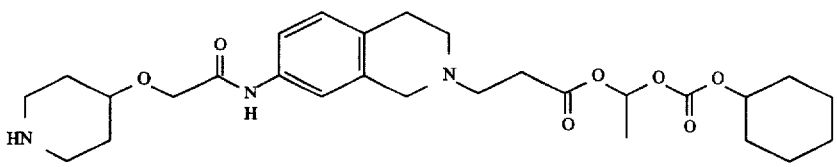

(34)

(Experiments)

Inhibity effects on human platelet of the invention derivatives to evaluate the activity for inhibiting aggregation induced by ADP (adenosine diphosphate), thrombin, and fibrinogen were measured in accordance with the procedure as described below.

(1) Preparation of platelet-rich plasma, washed platelets, and α-chymotrypsin-treated platelets Human whole blood withdrawn from human elbow vein into 10% volume of 3.8% sodium citrate was centrifuged at 135×g (1100 rpm) for 10 minutes, and the supernatant was collected as platelet-rich plasma (PRP). The residue was further centrifuged at 1600×g (3000 rpm) for 10 minutes, and the supernatant was collected as platelet-poor plasma (PPP). PRP and PPP were used for the measurement of the aggregation induced by ADP. In the meanwhile, PRP was applied to Sepharose CL-2B column (manufacture by Pharmacia) equilibrated with HEPES buffer, pH 7.4 containing 0.5% BSA and 5.5 mM glucose, and the fractions eluted in the void volume were collected as platelet-suspension, and used for the measurement of the aggregation induced by thrombin. In addition, washed platelet were treated with α-chymotrypsin of the final concentration of 10 U/ml for 30 minutes at room temperature. Then, the protease reaction was stopped by the addition of trypsin-chymotrypsin inhibitor (0.5 mg/ml), and α-chymotrypsin-treated platelet-suspension was used for the aggregation induced by fibrinogen.

(2) Measurement of ADP-induced aggregation

PRP was diluted with PPP to adjust the number of platelets to 20 to 30×1e4/μl, and the aggregation induced by ADP was measured with aggligometer (HEMATRACER VI, manufactured by NBS). 0.2 ml of PRP was placed in the cubette of the aggligometer with 25 μl of the test solution or physiological saline (control), and was incubated at 37° C. for 5 minutes with stirring (1000 rpm). Then, 25 μl of ADP solution was added and the time course of the light transmittance was recorded. The transmittance of PRP and PPP were calibrated as 0 and 100% respectively, and the maximum transmittance after adding the agonist was taken for the maximum aggregation. The concentration of 50% inhibition (IC$_{50}$) was calculated from the proportion of the maximum aggregation with test solution to physiological saline.

Results are shown in Table 1.

(3) Measurement of thrombin-induced aggregation

The platelet-suspension was diluted with HEPES buffer, pH 7.4 to adjust the number of platelets to 20 to 30×1e4/μl, and calcium chloride and magnesium chloride were respectively added to 2 mM (final concentration). The aggregation induced by thrombin was measured with this platelet-suspension and HEPES buffer (contrast) by the same procedure as the measurement of the aggregation induced by the ADP. The concentration of 50% inhibition (IC$_{50}$) was calculated from the proportion of the maximum aggregation with test solution to physiological saline.

Results are shown in Table 1.

(4) Measurement of fibrinogen-induced aggregation

α-chymotrypsin-treated platelet-suspension was diluted with HEPES buffer, pH 7.4 to adjust the number of platelets to 20 to 30×1e4/μl. Calcium chloride and magnesium chloride were respectively added to 2 mM (final concentration), and PGE1 was added to 1 μM (final concentration). The aggregation induced by fibrinogen (0.4 mg/ml) was measured with this platelet-suspension and the HEPES buffer (contrast). The concentration of 50% inhibition (IC$_{50}$) was calculated from the proportion of the maximum aggregation with test solution to physiological saline.

Results are shown in Table 1.

(5) Measurement of bioavailability (rat)

Bioavailability upon administration of the compound of Example 4-1 (formula 15) was evaluated by measuring the compound of Example 2 (formula 13), which is the hydrolysis product of the ester. It was then found that the bioavailability was 13%.

TABLE 1

| Compound | Inhibitory action for agglutination by | | |
|---|---|---|---|
| | ADP IC$_{50}$ (μM) | thrombin IC$_{50}$ (μM) | fibrinogen IC$_{50}$ (μM) |
| Ex. 1 (formula 12) | 5.0 | 4.8 | — |
| Ex. 2 (formula 13) | 0.097 | 0.066 | 0.038 |
| Ex. 3 (formula 14) | >10 | >10 | — |
| Ex. 5 (formula 19) | 81 | 43 | — |
| Ex. 6 (formula 20) | 2.9 | 1.9 | — |
| Ex. 7 (formula 21) | >10 | — | — |
| Ex. 8 (formula 22) | 0.23 | — | — |
| Ex. 9 (formula 23) | 0.32 | — | — |
| Ex. 10 (formula 24) | 0.38 | — | — |
| Ex. 11 (formula 25) | 0.15 | — | — |
| Ex. 12 (formula 26) | 12 | — | — |

(Acute toxicity)

Acute toxicity of the tetrahydroisoquinoline derivatives of the present invention was evaluated by using ICR male mice (5 weeks). Since LD$_{50}$ was higher than 300 mg in all cases, the high safety of the tetrahydroisoquinoline derivatives was confirmed.

Industrial Utility

As described above, novel tetrahydroisoquinoline derivatives are provided by the present invention. The tetrahydroisoquinoline derivatives of the present invention exhibit inhibitory action in aggregation induced by fibrinogen as demonstrated in Experiments. Therefore, these compound are effective as therapeutic and prophylactic agents for diseases having involved therewith platelet aggregation caused by the binding of the fibrinogen or other adhesive protein to GPIIb/IIIa receptor. The tetrahydroisoquinoline derivatives of the present invention are particularly useful as antithrombotic agents.

We claim:
1. A tetrahydroisoquinoline compound represented by the formula (I):

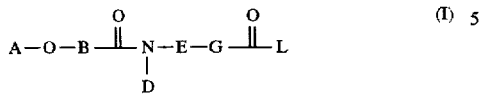

wherein:
(1) B is optionally not present and, if not present, then N is attached to A- via a carboxyl group and
(2) G is optionally not present and, if not present, then E is attached to L via a carboxyl group; and further wherein B and G are independently selected from an alkylene having 1-10 carbons wherein said alkylene may optionally contain substituents which are selected from the group consisting of:
 (a) an alkyl having 1-10 carbon atoms, aryl, amine, hydroxyl, and halogen;
 (b) —$R^1$—$R^2$ wherein $R^1$ is an alkylene having 1-8 carbon atoms and $R^2$ is an aryl group;
 (c) —NH—(C=O)—$R^3$ wherein $R^3$ is an alkyl having 1-10 carbon atoms;
 (d) —NH—$R^4$ wherein $R^4$ is (i) an alkyl having 1-10 carbon atoms or an aryl or (ii) —$R^5$—$R^6$ wherein $R^5$ is an alkylene having 1-8 carbon atoms and $R^6$ is an aryl group; and
 (e) —O—$R^7$ wherein $R^7$ is (i) an alkyl having 1-10 carbon atoms or (ii) —$R^8$—$R^9$ wherein $R^8$ is an alkylene having 1-8 carbon atoms and $R^9$ is an aryl group; and D is selected from the group consisting of:
 (f) hydrogen, an alkyl having 1-10 carbon atoms and arylcarbonyl;
 (g) —C(C=O)—O—$R^{10}$ wherein $R^{10}$ is (i) an alkyl having 1-10 carbon atoms or (ii) —$R^{11}$—$R^{12}$ wherein $R^{11}$ is an alkylene having 1-8 carbon atoms and $R^{12}$ is an aryl; and
 (h) —C(C=O)—O—$R^{15}$—O—(C=O)—$R^{16}$ wherein $R^{15}$ is an alkylene having 1-10 carbon atoms and $R^{16}$ is (i) an alkyl having 1-10 carbon atoms or an aryl group or (ii) —$R^{17}$—$R^{18}$ wherein $R^{17}$ is an alkylene having 1-10 carbon atoms and $R^{18}$ is aryl; and E is a 1,2,3,4-tetrahydroisoquinoline which is attached to G at position 2 and to N at any of positions 5, 6, 7 or 8, wherein said tetrahydroisoquinoline optionally may be substituted with one or more substituents selected from the group consisting of:
 (i) an alkyl having 1-10 carbon atoms, aryl, hydroxyl, amine and halogen;
 (j) —$R^{19}$—$R^{20}$ wherein $R^{19}$ is an alkylene having 1-8 carbon atoms and $R^{20}$ is an aryl group;
 (k) —NH—(C=O)—$R^{21}$ wherein $R^{21}$ is an alkyl having 1-10 carbon atoms;
 (l) —NH—$R^{22}$ wherein $R^{22}$ is (i) an alkyl having 1-10 carbon atoms or aryl or (ii) —$R^{23}$—$R^{24}$ wherein $R^{23}$ is an alkylene having 1-8 carbon atoms and $R^{24}$ is an aryl group; and
 (m) —O—$R^{25}$ wherein $R^{25}$ is (i) an alkyl having 1-10 carbon atoms or (ii) —$R^{26}$—$R^{27}$ wherein $R^{26}$ is an alkylene having 1-8 carbon atoms and $R^{27}$ is an aryl group; and L is selected from the group consisting of:
 (n) hydroxyl, amine and aryl;
 (o) —NH—$R^{28}$ wherein $R^{28}$ is (i) an alkyl having 1-10 carbon atoms or (ii) —$R^{29}$—$R^{30}$ wherein $R^{29}$ is an alkylene having 1-10 carbon atoms and $R^{30}$ is an aryl group;
 (p) —$NR^{31}$ ($R^{32}$) wherein $R^{31}$ and $R^{32}$ are independently selected from alkyls having 1-10 carbon atoms;
 (q) —O—$R^{33}$ wherein $R^{33}$ is (i) an alkyl having 1-10 carbon atoms or (ii) —$R^{34}$—$R^{35}$ wherein $R^{34}$ is an alkylene having 1-8 carbon atoms and $R^{35}$ is an aryl group; and
 (r) —O—$R^{36}$—O—(C=O)—$R^{37}$ wherein $R^{36}$ is an alkylene having 1-10 carbon atoms and $R^{37}$ is (i) an alkyl having 1-10 carbon atoms or (ii) $R^{38}$—$R^{39}$ wherein $R^{38}$ is an alkylene having 1-10 carbon atoms and $R^{39}$ is an aryl; and A is a piperidine derivative of the Formula (II) which is attached at the 2, 3 or 4 position to —O— of the compound represented by Formula (II).

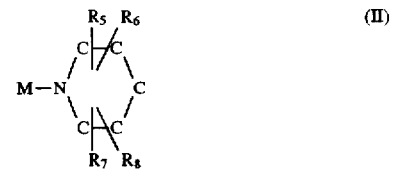

wherein M is selected from the same substituents as D, and $R_5$, $R_6$, $R_7$ and $R_8$ are independently selected from the group consisting of:
 (s) hydrogen, an alkyl having 1-10 carbon atoms, aryl, amine, hydroxyl and halogen;
 (t) —$R^{40}$—$R^{41}$ wherein $R^{40}$ is an alkylene having 1-10 carbon atoms and $R^{41}$ is an aryl;
 (u) —NH—$R^{42}$ wherein $R^{42}$ is (i) an alkyl having 1-10 carbon atoms or (ii) —$R^{43}$—$R^{44}$ wherein $R^{43}$ is a carbonyl and $R^{44}$ is an alkyl having 1-10 carbon atoms; and
 (v) —O—$R^{45}$ wherein $R^{45}$ is (i) an alkyl having 1-10 carbon atoms or (ii) —$R^{46}$—$R^{47}$ wherein $R^{46}$ is an alkylene having 1-8 carbon atoms and $R^{47}$ is an aryl group.

2. The tetrahydroisoquinoline derivative according to claim 1, wherein:
B and G are independently selected from (C:1-5) having 1-5 carbon atoms;
D is hydrogen or an alkyl having 1-5 carbon atoms;
E is unsubstituted or contains a substituent on the tetrahydroisoquinoline moiety which is selected from the group consisting of alkyls having 1-5 carbon atoms and phenyl;
L is selected from the group consisting of hydroxyl, —O—$R^{33}$ and —O—$R^{36}$—O—(C=O)—$R^{37}$, wherein $R^{33}$, $R^{36}$ and $R^{37}$ are as defined in claim 3;
A is attached at the 4 position to —O—, wherein M is selected from the group consisting of hydrogen, an alkyl carbonyl (alkyl has 1-5 carbon atoms), and $R_5$, $R_6$, $R_7$ and $R_8$ independently are selected from hydrogen or an alkyl having 1-5 carbon atoms.

3. The tetrahydroisoquinoline derivative according to claim 2, wherein:
D is hydrogen or methyl;
E is unsubstituted or contains an alkyl substituent having 1-5 carbon atoms;
L is hydroxyl or ethoxyl,
M is hydrogen, and
$R_5$ $R_6$, $R_7$ and $R_8$ are each hydrogen.

4. The tetrahydroisoquinoline derivative according to claim 1, wherein:

D is hydrogen; and

E is unsubstituted or contains a methyl substituent.

5. A tetrahydroisoquinoline compound according to claim 1 which is selected from the group consisting of:

2-(ethoxycarbonylmethyl)-7-nitro-1,2,3,4-tetrahydroisoquinoline;

7-(piperidine-4-yloxyacetyl-amino)-2-carboxymethyl-1,2,3,4-tetrahydroisoquinoline;

7-(piperidine-4-yloxyacetylamino)-2-carboxyethyl-1,2,3,4-tetrahydroisoquinoline;

7-(piperidine-4-yloxyacetylamino)-2-(3-carboxypropyl)-1,2,3,4-tetrahydroisoquinoline;

7-(piperidine-4-yloxyacetylamino)-2-(2-(ethoxycarbonyl)ethyl)-1,2,3,4-tetrahydroisoquinoline;

7-(piperidine-4-yloxyacetylamino)-2-(2-ethoxycarbonyl)ethyl)-1,2,3,4-tetrahydroisoquinoline 2 tosylate;

7-(piperidine-4-yloxyacetylamino)-2-(2-(ethoxycarbonyl)ethyl)-1,2,3,4-tetrahydroisoquinoline maleate;

7-(piperidine-4-yloxyacetylamino)-2-(2-(ethoxycarbonyl)ethyl)-1,2,3,4-tetrahydroisoquinoline 2 mesylate;

7-[(piperidine-4-yloxy-acetyl)methylamino]-2-[2-(carboxy)-ethyl]-1,2,3,4-tetrahydroisoquinoline;

2-(carbonylethyl)-1-phenyl-7-(piperidine-4-yloxyacetylamino)-1,2,3,4-tetrahydroisoquinoline;

7-(2,6-dimethylpiperidine-4-yloxyacetylamino)-2-(2-carboxyethyl)-1,2,3,4-tetrahydroisoquinoline;

7-(3-methylpiperidine-4-yloxyacetylamino)-2-(2-carboxyethyl)-1,2,3,4-tetrahydroisoquinoline;

7-(piperidine-4-yloxyacetylamino)-2-(2-carboxy-1-methylethyl)-1,2,3,4-tetrahydroisoquinoline;

2-(2-carboxyethyl)-1-methyl-7-(piperidine-4-yloxyacetylamino)-1,2,3,4-tetrahydroisoquinoline hydrochloride;

2-(2-carboxyethyl)-4-methyl-7-(piperidine-4-yloxyacetyl-amino)-1,2,3,4-tetrahydroisoquinoline hydrochloride;

2-(2-carboxy-ethyl)-3,3-dimethyl-7-(piperidine-4-yloxyacetylamino)-1,2,3,4-tetrahydroisoquinoline hydrochloride;

7-((N-(acetoxymethoxycarbonyl)piperidine)-4-yloxyacetylamino)-2-(2-(ethoxycarbonyl)ethyl)-1,2,3,4-tetrahydroisoquinoline hydrochloride;

7-((N-(1-acetoxy)ethoxy-carbonyl)piperidine)-4-yloxyacetylamino)-2-(2-ethoxy-carbonyl)ethyl)-1,2,3,4-tetrahydroisoquinoline;

7-((N-(pivaloyloxymethoxycarbonyl)piperidine)-4-yloxyacetylamino)-2-(2-(ethoxycarbonyl)ethyl)-1,2,3,4-tetrahydroisoquinoline toluenesulfonate;

7-((N-(hexyloxy-carbonyl)piperidine)-4-yloxyacetylamino)-2-(2-(ethoxy-carbonyl)ethyl-1,2,3,4-tetrahydroisoquinoline hydrochloride;

7-[1-(acetoxymethoxycarbonyl)piperidine-4-yloxylacetylamino]-2-(2-carboxyethyl)-1,2,3,4-tetrahydroisoquinoline;

7-(piperidine-4-yloxyacetylamino)-2-(2-(isopropyloxycarbonyl)-ethyl)-1,2,3,4-tetrahydroisoquinoline tosylate;

7-(piperidine-4-yloxyacetylamino)-2-(2-pivaloyloxymethoxycarbonyl)ethyl)-1,2,3,4-tetrahydroisoquinoline di-hydrobromate; and 7-(piperidine-4-yloxyacetylamino)-2-(2-(1-(cyclohexyloxycarbonyloxy)ethoxycarbonyl)ethyl)-1,2,3,4-tetrahydroisoquinoline di-hydrobromate.

6. A pharmaceutical composition comprising a pharmaceutically effective amount of at least one tetrahydroisoquinoline compound according to claim 1, and a pharmaceutically acceptable carrier.

7. A pharmaceutical composition containing at least one compound according to claim 2, and a pharmaceutically acceptable carrier.

8. A pharmaceutical composition containing at least one compound according to claim 3, and a pharmaceutically acceptable carrier.

9. A pharmaceutical composition containing at least one compound according to claim 4, and a pharmaceutically acceptable carrier.

10. A pharmaceutical composition containing at least one compound according to claim 5, and a pharmaceutically acceptable carrier.

* * * * *

UNITED STATES PATENT AND TRADEMARK OFFICE
CERTIFICATE OF CORRECTION

PATENT NO. : 5,789,595
DATED : August 4, 1998
INVENTOR(S) : Hiromasa Kohama, et al.

It is certified that error appears in the above-identified patent and that said Letters Patent is hereby corrected as shown below:

In column 16, line 9, delete "aluminum lithium" and insert --lithium aluminum--.
In column 20, line 11, delete "ref lux" and insert --reflux--.
In column 22, line 48, delete "(".
In columns 27 and 28, delete

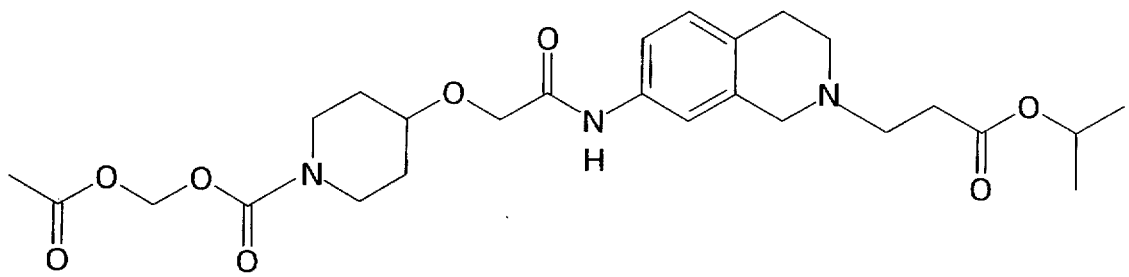

(31)

and insert:

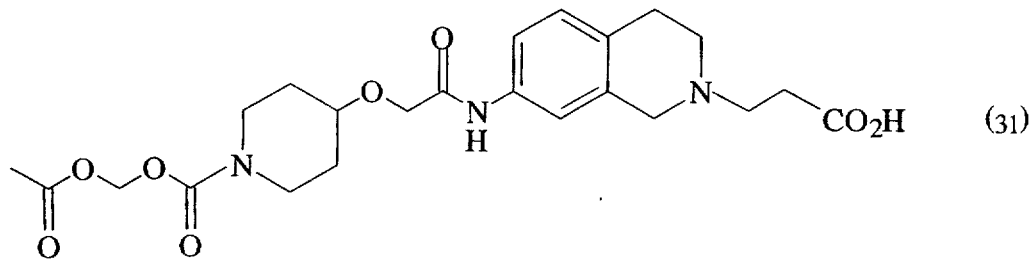

(31)

UNITED STATES PATENT AND TRADEMARK OFFICE
CERTIFICATE OF CORRECTION

PATENT NO. : 5,789,595

DATED : August 4, 1998

INVENTOR(S) : Hiromasa Kohama, et al.

It is certified that error appears in the above-identified patent and that said Letters Patent is hereby corrected as shown below:

In column 29, delete

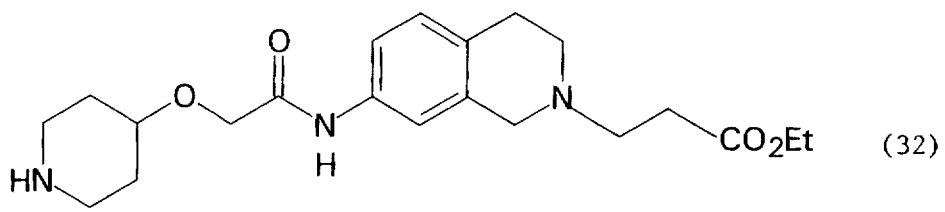

(32)

and insert:

UNITED STATES PATENT AND TRADEMARK OFFICE
CERTIFICATE OF CORRECTION

PATENT NO. : 5,789,595 -
DATED : Hiromasa Kohama, et al.
INVENTOR(S) : August 4, 1998

It is certified that error appears in the above-identified patent and that said Letters Patent is hereby corrected as shown below:

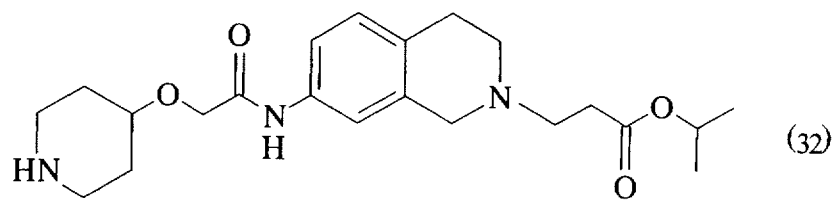

(32)

Signed and Sealed this

Thirtieth Day of November, 1999

*Attest:*

*Attesting Officer*

Q. TODD DICKINSON

*Acting Commissioner of Patents and Trademarks*